United States Patent
Takano et al.

(10) Patent No.: US 12,150,727 B2
(45) Date of Patent: Nov. 26, 2024

(54) ROBOTIC SURGICAL SYSTEM, OPERATOR-SIDE APPARATUS, AND CONTROL METHOD OF ROBOTIC SURGICAL SYSTEM

(71) Applicant: KAWASAKI JUKOGYO KABUSHIKI KAISHA, Kobe (JP)

(72) Inventors: Yusuke Takano, Kobe (JP); Takeshi Kurihara, Kobe (JP); Masataka Tanabe, Kobe (JP); Shinji Kajihara, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 293 days.

(21) Appl. No.: 17/875,487

(22) Filed: Jul. 28, 2022

(65) Prior Publication Data
US 2023/0034631 A1    Feb. 2, 2023

(30) Foreign Application Priority Data
Jul. 30, 2021    (JP) .................................. 2021-126022

(51) Int. Cl.
*A61B 34/37*    (2016.01)
*A61B 34/00*    (2016.01)
*B25J 13/06*    (2006.01)

(52) U.S. Cl.
CPC .............. *A61B 34/37* (2016.02); *A61B 34/25* (2016.02); *A61B 34/77* (2016.02); *B25J 13/06* (2013.01)

(58) Field of Classification Search
CPC ......... A61B 34/25; A61B 24/37; A61B 34/77; A61B 2017/00973; A61B 2034/2059; B25J 9/0087; B25J 9/1689; B25J 13/025; B25J 13/04; B25J 13/06; G05B 2219/45123
See application file for complete search history.

(56) References Cited

U.S. PATENT DOCUMENTS

| | | | |
|---|---|---|---|
| 2004/0243110 A1 | 12/2004 | Niemeyer | |
| 2009/0247993 A1* | 10/2009 | Kirschenman | A61B 34/71 606/1 |
| 2018/0250086 A1* | 9/2018 | Grubbs | A61B 34/35 |
| 2019/0059985 A1* | 2/2019 | Shelton, IV | A61B 17/07207 |
| 2020/0237456 A1* | 7/2020 | Prisco | A61B 34/30 |
| 2022/0110705 A1* | 4/2022 | Hourtash | A61B 34/30 |
| 2023/0149105 A1* | 5/2023 | Thornycroft | A61B 34/77 606/45 |

FOREIGN PATENT DOCUMENTS

JP    2021-023705 A    2/2021

* cited by examiner

*Primary Examiner* — Jason Holloway
*Assistant Examiner* — Blake A Wood
(74) *Attorney, Agent, or Firm* — METROLEX IP LAW GROUP, PLLC; Robert L. Scott, Esq.

(57) ABSTRACT

In a robotic surgical system, a controller is configured or programmed to change at least one of a level of an operation start assisting force, a level of an in-operation assisting force, or a level of a braking force based on a level change operation of an operator received by a level change receiver.

20 Claims, 24 Drawing Sheets

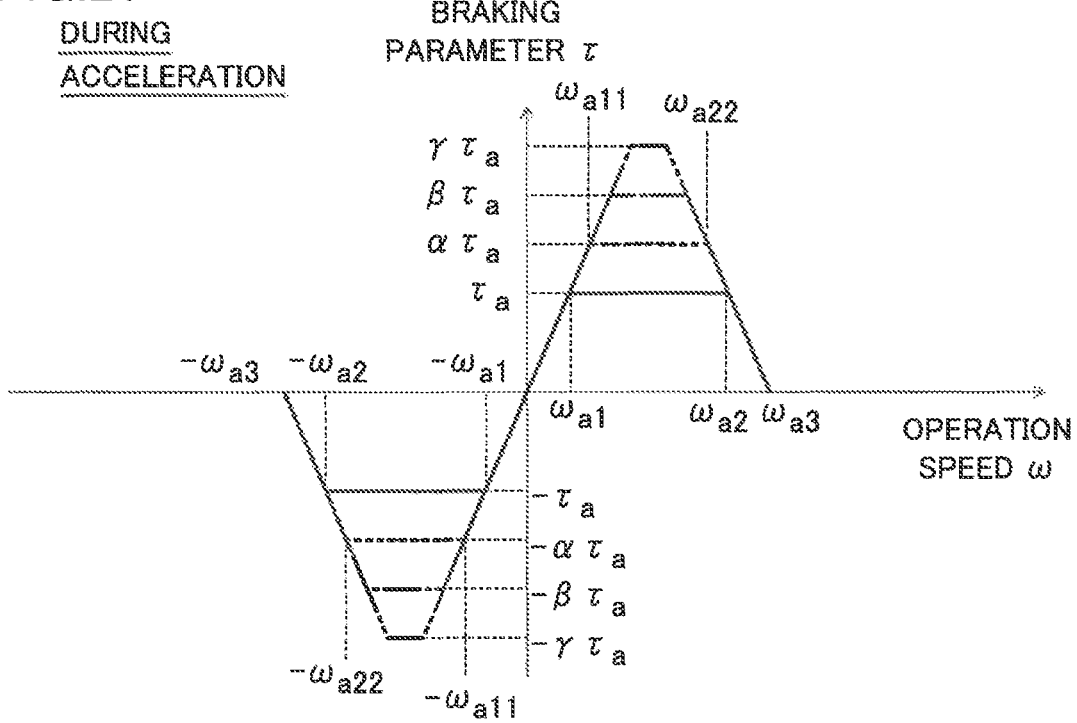
FIG.21 DURING ACCELERATION
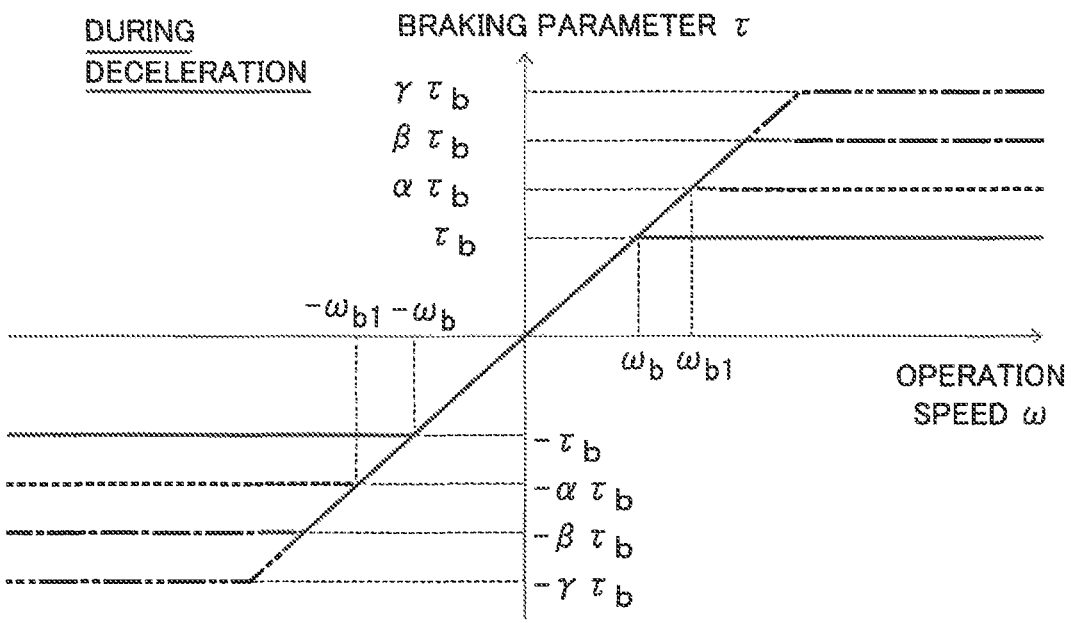
FIG.22 DURING DECELERATION

ROBOTIC SURGICAL SYSTEM, OPERATOR-SIDE APPARATUS, AND CONTROL METHOD OF ROBOTIC SURGICAL SYSTEM

CROSS-REFERENCE TO RELATED APPLICATION

The present application claims priority to JP2021-126022, which is incorporated herein by reference.

BACKGROUND OF THE INVENTION

Field of the Invention

The present disclosure relates to a robotic surgical system, an operator-side apparatus, and a control method of a robotic surgical system, and more particularly, it relates to a robotic surgical system and an operator-side apparatus each including an operation unit to receive an operation of an operator, and a control method of the robotic surgical system.

Description of the Background Art

Conventionally, a robotic surgical system including an operation unit to receive an operation of an operator is known. For example, a technology that controls movement of a surgical instrument provided on an articulated robot arm as a slave based on the amount of operation received by an operation unit provided in a master control device is disclosed in U.S. Patent Application Publication No. 2004/0243110. In U.S. Patent Application Publication No. 2004/0243110, a tool moves within the patient's body, which is a surgical site.

In U.S. Patent Application Publication No. 2004/0243110, the operation unit provided in the master control device includes an articulated arm including a plurality of links. The articulated arm is suspended from above while being bent in an L shape. The articulated arm includes a motor. The motor located in the articulated arm generates a torque to resist the gravity. Even when an operator does not support the operation unit by hand, the torque generated by the motor maintains the L-shaped bent state of the articulated arm.

In U.S. Patent Application Publication No. 2004/0243110, the motor generates a force according to an operation speed at which the operator operates the operation unit. The force generated by the motor assists the operation of the operator on the operation unit. The operation on the operation unit is assisted such that a force required to operate the operation unit becomes small.

When the operation on the operation unit is assisted as in the U.S. Patent Application Publication No. 2004/0243110, the appropriate amount of force that assists the operation on the operation unit varies depending on the operator. In the U.S. Patent Application Publication No. 2004/0243110, the amount of assisting force may not be appropriate for the operator.

SUMMARY OF THE INVENTION

The present disclosure is intended to solve the above problem. The present disclosure aims to provide a robotic surgical system, an operator-side apparatus, and a control method of a robotic surgical system each capable of appropriately assisting an operation on an operation unit according to an operator.

In order to attain the aforementioned object, a robotic surgical system according to a first aspect of the present disclosure includes a patient-side apparatus including a manipulator arm having a tip end to which a surgical instrument is attached, an operator-side apparatus including an operation unit to receive an operation of an operator, a controller, and a level change receiver to receive a level change operation of the operator. The operation unit includes a drive to assist the operation of the operator, the controller is configured or programmed to control the drive to exert at least one of an operation start assisting force exerted when the operation unit starts to be operated, an in-operation assisting force exerted when the operation unit is being operated, or a braking force exerted when the operation unit is stopped, and the controller is configured or programmed to change at least one of a level of the operation start assisting force, a level of the in-operation assisting force, or a level of the braking force based on the level change operation of the operator received by the level change receiver.

In the robotic surgical system according to the first aspect of the present disclosure, as described above, the controller is configured or programmed to change at least one of the level of the operation start assisting force, the level of the in-operation assisting force, or the level of the braking force based on the level change operation of the operator received by the level change receiver. Accordingly, the operator can change at least one of the level of the operation start assisting force, the level of the in-operation assisting force, or the level of the braking force to a desired level by the level change operation. Therefore, an operation on the operation unit can be appropriately assisted according to the operator.

An operator-side apparatus according to a second aspect of the present disclosure operates a patient-side apparatus including a manipulator arm having a tip end to which a surgical instrument is attached, and includes an operation unit to receive an operation of an operator, a controller, and a level change receiver to receive a level change operation of the operator. The operation unit includes a drive to assist the operation of the operator, the controller is configured or programmed to control the drive to exert at least one of an operation start assisting force exerted when the operation unit starts to be operated, an in-operation assisting force exerted when the operation unit is being operated, or a braking force exerted when the operation unit is stopped, and the controller is configured or programmed to change at least one of a level of the operation start assisting force, a level of the in-operation assisting force, or a level of the braking force based on the level change operation of the operator received by the level change receiver.

In the operator-side apparatus according to the second aspect of the present disclosure, as described above, the controller is configured or programmed to change at least one of the level of the operation start assisting force, the level of the in-operation assisting force, or the level of the braking force based on the level change operation of the operator. Accordingly, the operator can change at least one of the level of the operation start assisting force, the level of the in-operation assisting force, or the level of the braking force to a desired level by the level change operation. Therefore, it is possible to provide the operator-side apparatus capable of appropriately assisting an operation on the operation unit according to the operator.

A control method of a robotic surgical system that includes a patient-side apparatus including a manipulator arm having a tip end to which a surgical instrument is attached and an operator-side apparatus including an operation unit to receive an operation of an operator according to a third aspect of the present invention includes receiving at least one of a change in a level of an operation start assisting force exerted when the operation unit starts to be operated, a change in a level of an in-operation assisting force exerted when the operation unit is being operated, or a change in a level of a braking force exerted when the operation unit is stopped, and exerting at least one of the operation start assisting force, the in-operation assisting force, or the braking force corresponding to a changed level.

As described above, the control method of the robotic surgical system according to the third aspect of the present invention includes receiving at least one of the change in the level of the operation start assisting force, the change in the level of the in-operation assisting force, or the change in the level of the braking force, and exerting at least one of the operation start assisting force, the in-operation assisting force, or the braking force corresponding to the changed level. Accordingly, the operator can change at least one of the level of the operation start assisting force, the level of the in-operation assisting force, or the level of the braking force to a desired level By the level change operation. Therefore, it is possible to provide the control method of the robotic surgical system capable of appropriately assisting an operation on the operation unit according to the operator.

According to the present disclosure, the operation on the operation unit can be appropriately assisted according to the operator.

The foregoing and other objects, features, aspects and advantages of the present disclosure will become more apparent from the following detailed description of the present disclosure when taken in conjunction with the accompanying drawings.

BRIEF DESCRIPTION OF THE DRAWINGS

FIG. 21 is a diagram showing a braking parameter during acceleration according to the first embodiment.

FIG. 22 is a diagram showing a braking parameter during deceleration according to the first embodiment.

DESCRIPTION OF THE PREFERRED EMBODIMENTS

Figure 1:
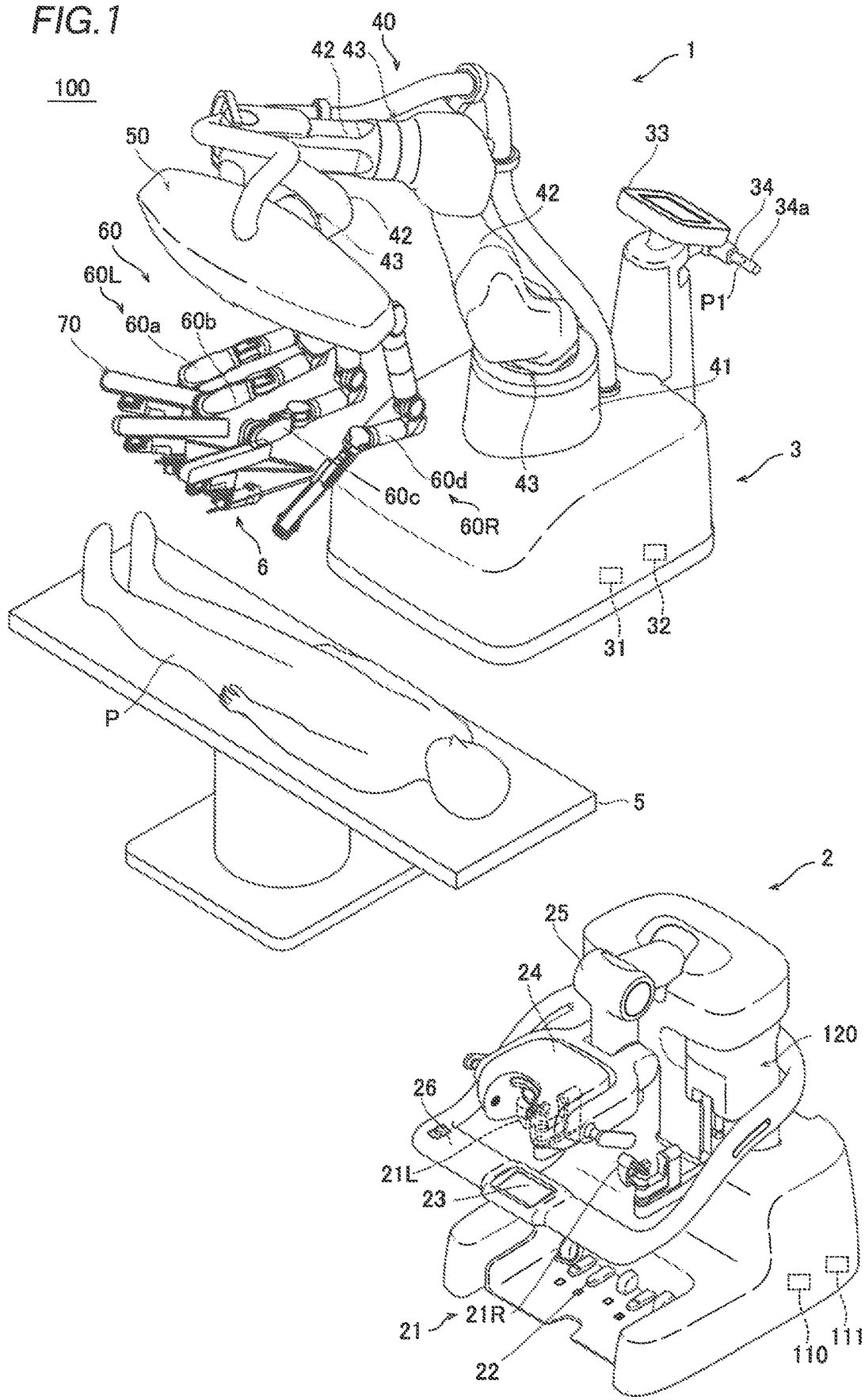
FIG. 1 is a diagram showing the configuration of a surgical system according to a first embodiment.

Embodiments of the present disclosure are hereinafter described with reference to the drawings.

First Embodiment

The configuration of a surgical system 100 according to a first embodiment is now described with reference to FIGS. 1 to 28. The surgical system 100 includes a medical manipulator 1 that is a patient P-side apparatus and a remote control apparatus 2 that is an operator-side apparatus to operate the medical manipulator 1. The medical manipulator 1 includes a medical cart 3 and is movable. The remote control apparatus 2 is spaced apart from the medical manipulator 1, and the medical manipulator 1 is remotely operated by the remote control apparatus 2. An operator such as a doctor inputs a command to the remote control apparatus 2 to cause the medical manipulator 1 to perform a desired operation. The remote control apparatus 2 transmits the input command to the medical manipulator 1. The medical manipulator 1 operates based on the received command. The medical manipulator 1 is arranged in an operating room that is a sterilized sterile field. The surgical system 100 is an example of a robotic surgical system. The medical manipulator 1 is an example of a patient-side apparatus. The remote control apparatus 2 is an example of an operator-side apparatus.

The remote control apparatus 2 is arranged inside or outside the operating room, for example. The remote control apparatus 2 includes an operation unit 120 including arms 121 shown in FIG. 3 and an operation handle 21, foot pedals 22, a touch panel 23, a monitor 24, a support arm 25, and a support bar 26. The operation unit 120 includes an operation handle for the operator such as a doctor to input a command.

Figure 3:
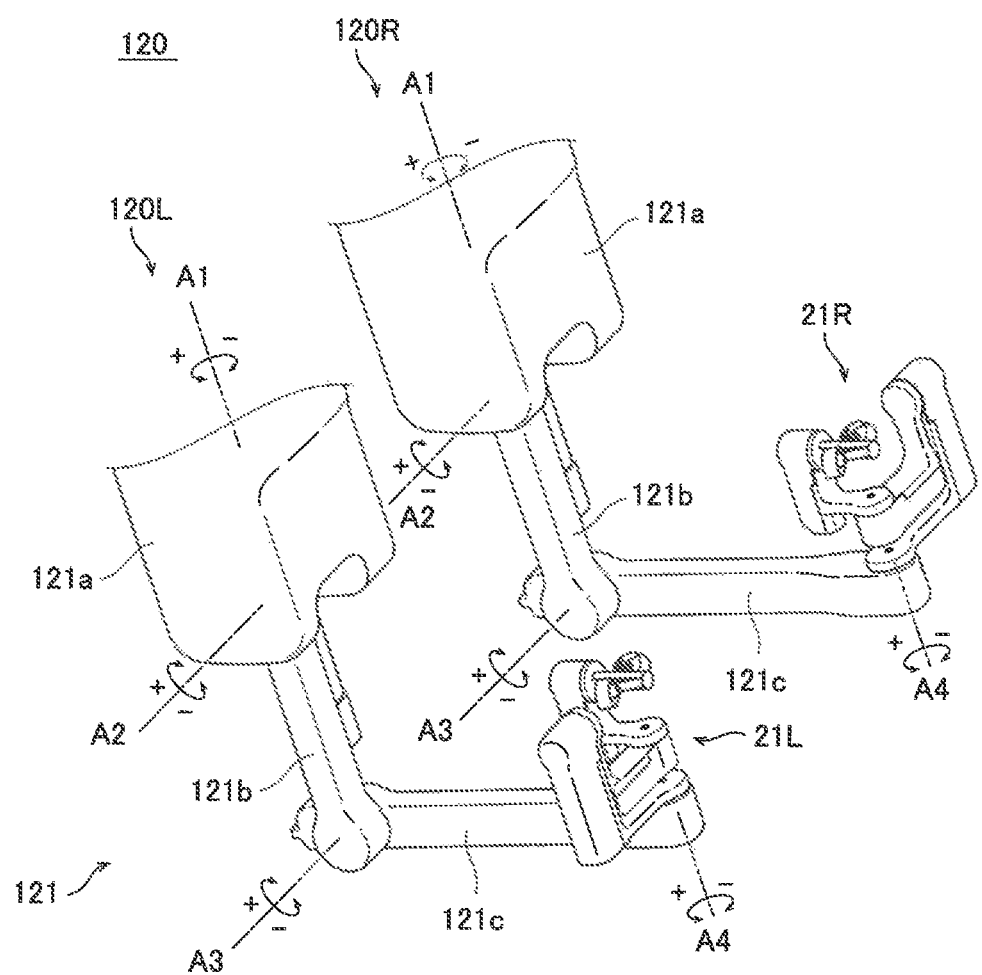
FIG. 3 is a perspective view showing the configuration of an operation unit of a remote control apparatus according to the first embodiment.

As shown in FIG. 3, the operation unit 120 includes an operation unit 120L located on the left side as viewed from the operator such as a doctor and operated by the operator's left hand, and an operation unit 120R located on the right side and operated by the operator's right hand. The configurations of the operation unit 120L and the operation unit 120R are the same as or similar to each other.

The operation unit 120 includes the substantially L-shaped arms 121. The arms 121 each have a first link 121*a*, a second link 121*b*, and a third link 121*c*. The upper end side of the first link 121*a* is attached to a main body of the remote control apparatus 2 such that the first link 121*a* is rotatable about an A1 axis along a vertical direction. The upper end side of the second link 121*b* is attached to the lower end side of the first link 121*a* such that the second link 121*b* is rotatable about an A2 axis along a horizontal direction. A first end side of the third link 121*c* is attached to the lower end side of the second link 121*b* such that the third link 121*c* is rotatable about an A3 axis along the horizontal direction. The operation handle 21 is attached to a second end side of the third link 121*c* such that the operation handle 21 is rotatable about an A4 axis.

The arms 121 each support the operation handle 21 such that the operation handle 21 is movable within a predetermined three-dimensional operation range. Specifically, the arm 121 supports the operation handle 21 such that the operation handle 21 is movable in an upward-downward direction, a right-left direction, and a forward-rearward direction. Manipulator arms 60 are moved three-dimensionally so as to correspond to the three-dimensional operations of the arms 121.

The operation handle 21 operates a surgical instrument 4. Furthermore, the operation handle 21 receives an operation amount for the surgical instrument 4. The operation handle 21 includes an operation handle 21L located on the left side as viewed from the operator such as a doctor and operated by the operator's left hand, and an operation handle 21R located on the right side and operated by the operator's right hand.

Figure 4:
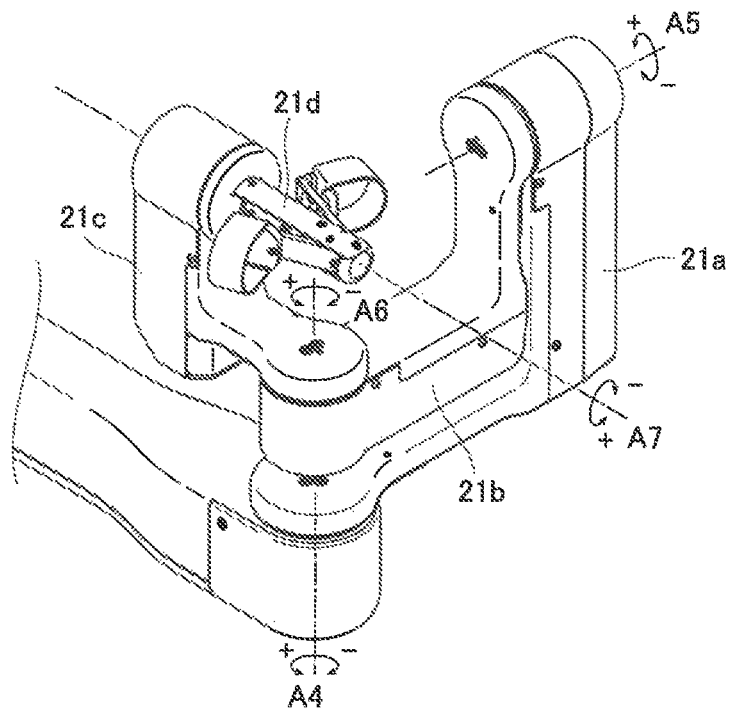
FIG. 4 is a diagram showing the configuration of an operation handle according to the first embodiment.

As shown in FIG. 4, the operation handle 21 includes a link 21*a*, a link 21*b*, a link 21*c*, and a link 21*d* operated by the operator such as a doctor. The link 21*a* rotates about the A4 axis. The link 21*b* rotates about an A5 axis with respect to the link 21*a*. The link 21*c* rotates about an A6 axis with respect to the link 21*b*. The link 21*d* rotates about an A7 axis with respect to the link 21*c*.

In the operation handle 21, the movement amounts of a manipulator arm 60 and the surgical instrument 4 are changed with respect to an operation amount received by the operation handle 21. This change is called scaling. For example, when the scale factor of the movement amounts is set to ½ times, the surgical instrument 4 is controlled to move ½ of the movement distance of the operation handle 21. Thus, fine surgery can be performed accurately.

Figure 5:
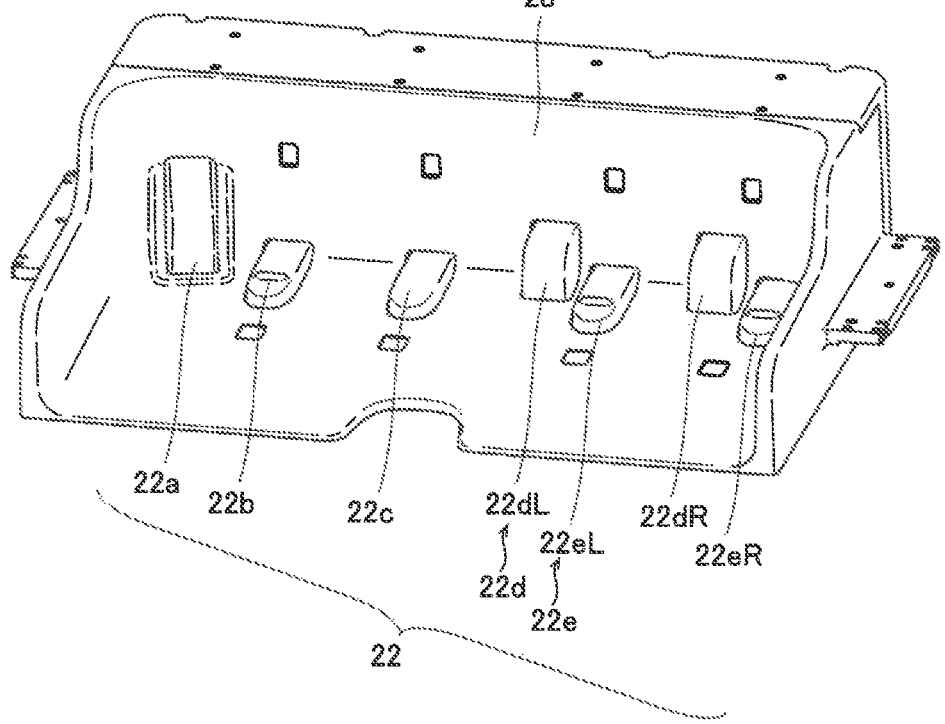
FIG. 5 is a diagram showing the configuration of foot pedals according to the first embodiment.

As shown in FIG. 5, a plurality of foot pedals 22 are provided to perform functions related to the surgical instrument 4. The plurality of foot pedals 22 are arranged on a base 28. The foot pedals 22 include a switching pedal 22*a*, a clutch pedal 22*b*, a camera pedal 22*c*, an incision pedal 22*d*, and a coagulation pedal 22*e*. The switching pedal 22*a*, the clutch pedal 22*b*, the camera pedal 22*c*, the incision pedal 22*d*, and the coagulation pedal 22*e* are operated by the operator's foot. The incision pedal 22*d* includes an incision pedal 22*d*R for a right manipulator arm 60, and an incision pedal 22*d*L for a left manipulator arm 60. The coagulation pedal 22*e* includes a coagulation pedal 22*e*R for the right manipulator arm 60 and a coagulation pedal 22*e*L for the left manipulator arm 60.

The switching pedal 22*a* switches a manipulator arm 60 to be operated by the operation handle 21. The clutch pedal 22*b* performs a clutch operation to temporarily disconnect an operation connection between the manipulator arm 60 and the operation handle 21. While the clutch pedal 22*b* is being pressed by the operator, an operation by the operation handle 21 is not transmitted to the manipulator arms 60. While the camera pedal 22*c* is being pressed by the operator, the operation handle 21 can operate a manipulator arm 60 to which an endoscope 6 is attached. While the incision pedal 22*d* or the coagulation pedal 22*e* is being pressed by the operator, an electrosurgical device is activated.

As shown in FIG. 1, the monitor 24 is a scope-type display that displays an image captured by the endoscope 6. The support arm 25 supports the monitor 24 so as to align the height of the monitor 24 with the height of the face of the operator such as a doctor. The touch panel 23 is arranged on the support bar 26. The operator's head is detected by a sensor provided in the vicinity of the monitor 24 such that the medical manipulator 1 can be operated by the remote control apparatus 2. The operator operates the operation handle 21 and the foot pedals 22 while visually recognizing an affected area on the monitor 24. Thus, a command is input to the remote control apparatus 2. The command input to the remote control apparatus 2 is transmitted to the medical manipulator 1.

The medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote control apparatus 2.

The medical cart 3 includes an input 33. The input 33 receives operations to move a positioner 40, an arm base 50, and a plurality of manipulator arms 60 or change their postures mainly in order to prepare for surgery before the surgery.

Figure 2:
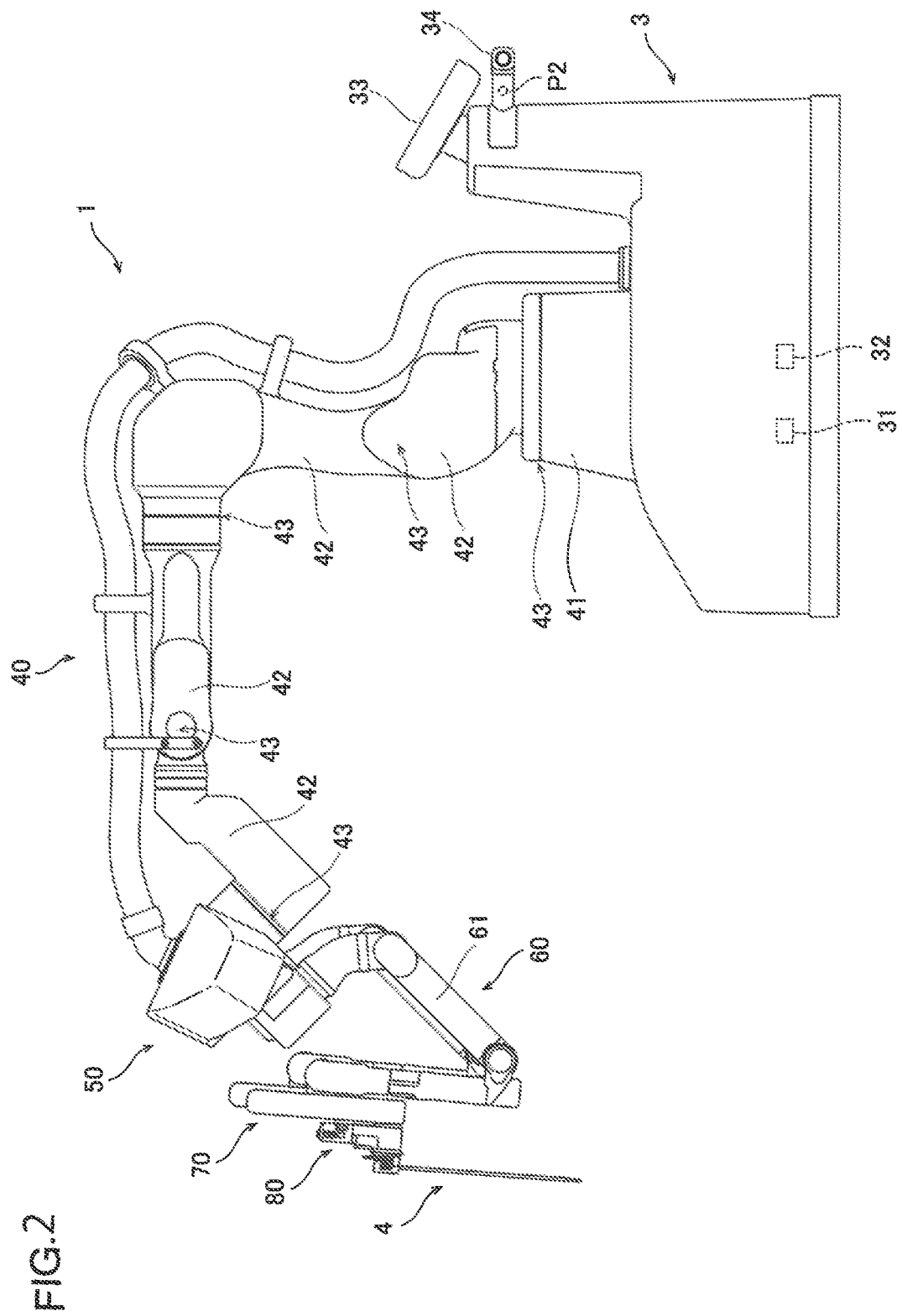
FIG. 2 is a diagram showing the configuration of a medical manipulator according to the first embodiment.

The medical manipulator 1 shown in FIGS. 1 and 2 is arranged in the operating room. The medical manipulator 1 includes the medical cart 3, the positioner 40, the arm base 50, and the plurality of manipulator arms 60. The arm base 50 is attached to the tip end of the positioner 40. The arm base 50 has a relatively long rod shape. That is, the arm base 50 has a long shape. The bases of the plurality of manipulator arms 60 are attached to the arm base 50. Each of the plurality of manipulator arms 60 is able to take a folded and stored posture. The arm base 50 and the plurality of manipulator arms 60 are covered with sterile drapes and used. The manipulator arms 60 support surgical instruments 4.

The positioner 40 includes a 7-axis articulated robot, for example. The positioner 40 is arranged on the medical cart 3. The positioner 40 moves the arm base 50. Specifically, the positioner 40 moves the position of the arm base 50 three-dimensionally.

The positioner 40 includes a base 41 and a plurality of links 42 coupled to the base 41. The plurality of links 42 are coupled to each other by joints 43.

As shown in FIG. 1, the surgical instrument 4 is attached to the tip end of each of the plurality of manipulator arms 60. The surgical instrument 4 includes a replaceable instrument or the endoscope 6 shown in FIG. 9 to capture an image of a surgical site, for example.

Figure 6:
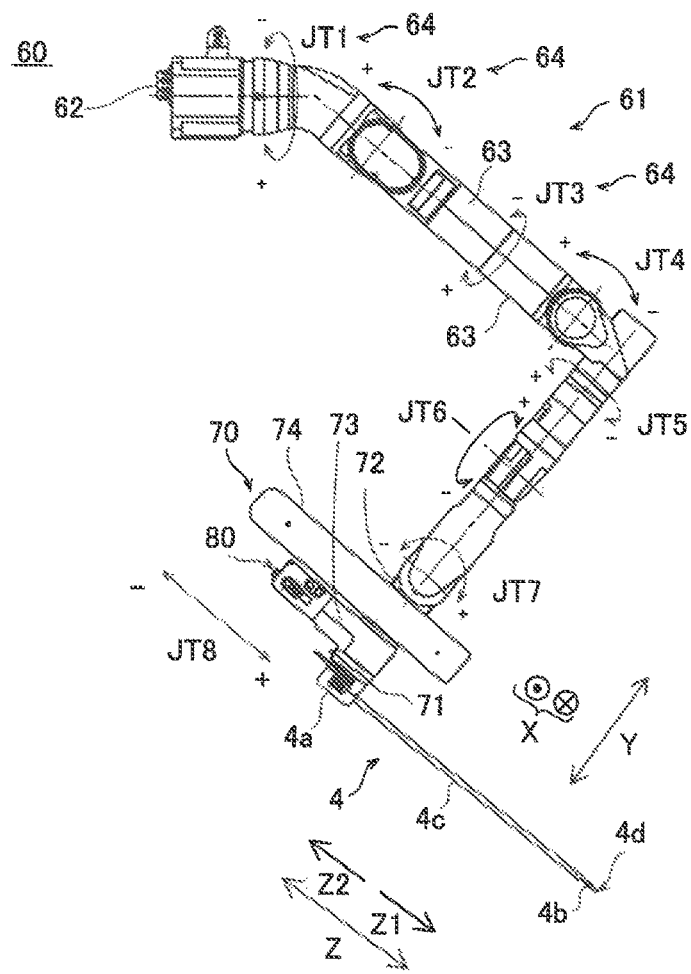
FIG. 6 is a diagram showing the configuration of a manipulator arm according to the first embodiment.

As shown in FIG. 6, the instrument includes a driven unit 4a driven by servomotors M2 provided in a holder 71 of each of the manipulator arms 60. A pair of forceps 4b is provided at the tip end of the instrument.

Figure 7:
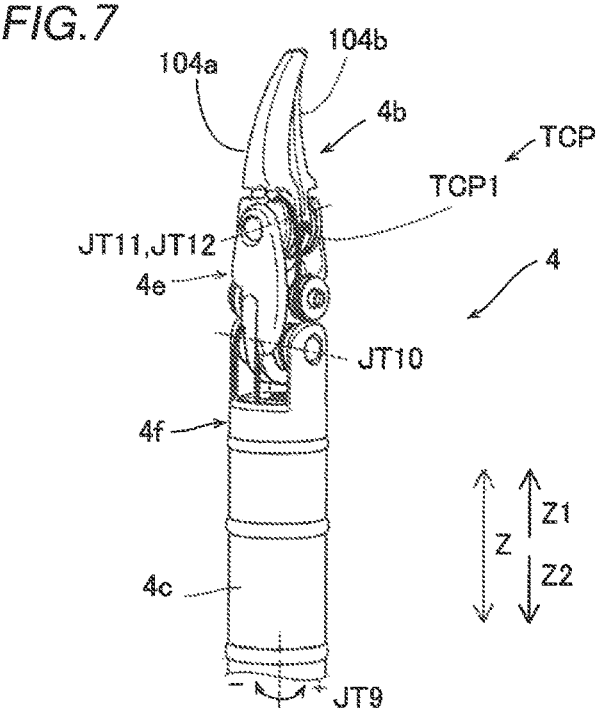
FIG. 7 is a diagram showing a pair of forceps.

As shown in FIG. 7, the instrument includes a first support 4e that supports the base end sides of end effector members 104a and 104b such that the base end sides of the end effector members 104a and 104b are rotatable about a JT11 axis on the tip end sides, a second support 4f that supports the base end side of the first support 4e such that the base end side of the first support 4e is rotatable about a JT10 axis on the tip end side, and a shaft 4c connected to the base end side of the second support 4f. The driven unit 4a, the shaft 4c, the second support 4f, the first support 4e, and the pair of forceps 4b are arranged along a Z direction. The JT11 axis is orthogonal to the Z direction in which the shaft 4c extends. The JT10 axis is spaced apart from the JT11 axis in the direction in which the shaft 4c extends, and is orthogonal to the direction in which the shaft 4c extends and the JT11 axis.

The pair of forceps 4b is attached to the first support 4e so as to rotate about the JT11 axis. The second support 4f supports the first support 4e such that the first support 4e is rotatable about the JT10 axis. That is, the first support 4e is attached to the second support 4f so as to rotate about the JT10 axis. A portion of the first support 4e on the Z1 direction side, which is the tip end side, has a U-shape. TCP1 is set as a tool center point at the center of the tip end of the U-shaped portion of the first support 4e in the JT11 axis.

The pair of forceps 4b as the surgical instrument 4 includes a JT9 axis as a rotation axis of the shaft 4c and a JT12 axis as an opening/closing axis of the pair of forceps 4b. The rotation axis of the shaft 4c is an axis along the direction in which the shaft 4c extends. A plurality of servomotors M2 are provided in the holder 71 of the manipulator arm 60, and rotary bodies of the driven unit 4a are driven by the plurality of servomotors M2. Thus, the surgical instrument 4 is driven around the JT9 axis to the JT12 axis. For example, four servomotors M2 are provided.

Figure 9:
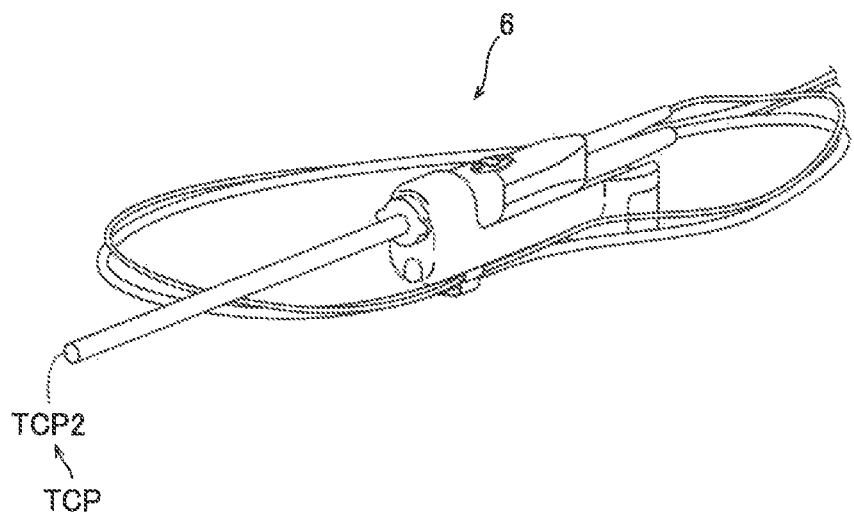
FIG. 9 is a diagram showing an endoscope.

As shown in FIG. 9, TCP2 of the endoscope 6 is set at the tip end of the endoscope 6.

The configuration of the manipulator arms 60 is now described in detail.

As shown in FIG. 6, each of the manipulator arms 60 includes an arm portion 61 and a translation mechanism 70 provided at the tip end of the arm portion 61. The arm portion 61 includes a base 62, links 63, and joints 64. The tip end sides of the manipulator arms 60 three-dimensionally move with respect to the arm base 50 on the base sides of the manipulator arms 60. The arm portion 61 includes a 7-axis articulated robot arm. The plurality of manipulator arms 60 have the same or similar configuration as each other.

Figure 13:
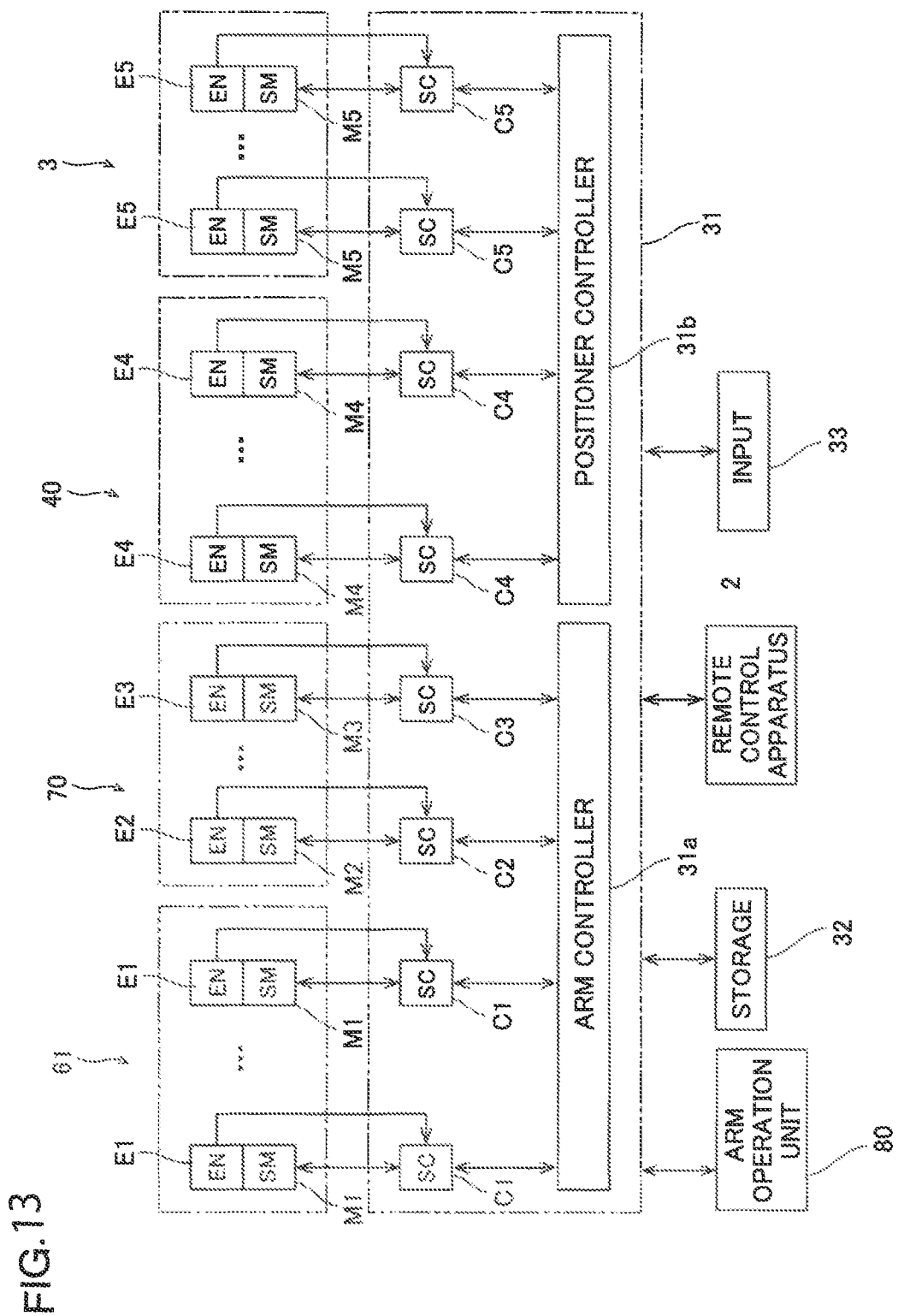
FIG. 13 is a block diagram showing the configuration of a controller of the medical manipulator according to the first embodiment.

As shown in FIG. 6, the manipulator arms 60 each include JT1 to JT7 axes as rotation axes and a JT8 axis as a linear motion axis. The JT1 to JT7 axes correspond to the rotation axes of the joints 64 of the arm portion 61. The JT7 axis corresponds to a base end side link 72 of the translation mechanism 70. The JT8 axis corresponds to an axis that moves a tip end side link 73 of the translation mechanism 70 relative to the base end side link 72 along the Z direction. That is, servomotors M1 shown in FIG. 13 are provided so as to correspond to the JT1 to JT7 axes of the manipulator arm 60. Furthermore, a servomotor M3 is provided so as to correspond to the JT8 axis.

The translation mechanism 70 is provided at the tip end of the arm portion 61, and the surgical instrument 4 is attached thereto. The translation mechanism 70 translates the surgical instrument 4 in a direction in which the surgical instrument 4 is inserted into the patient P. Furthermore, the translation mechanism 70 translates the surgical instrument 4 relative to the arm portion 61. Specifically, the translation mechanism 70 includes the holder 71 that holds the surgical instrument 4. The servomotors M2 shown in FIG. 13 are housed in the holder 71.

Figure 8:
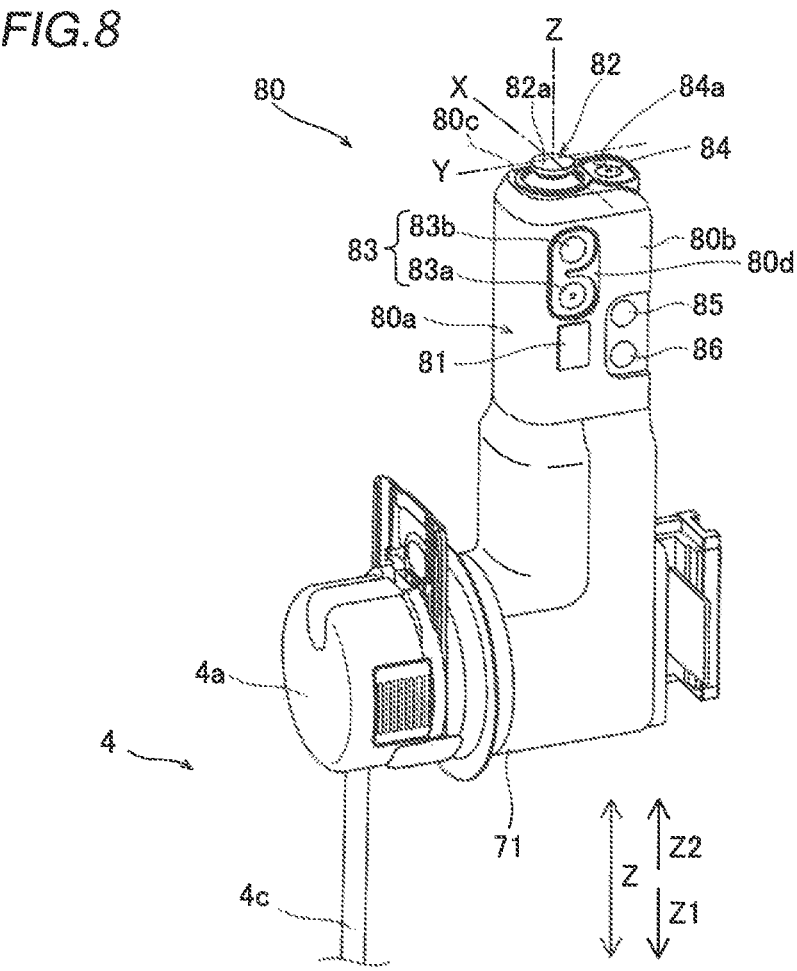
FIG. 8 is a perspective view showing the configuration of an arm operation unit of the medical manipulator according to the first embodiment.

As shown in FIG. 8, the medical manipulator 1 includes an arm operation unit 80 attached to each of the manipulator arms 60 to operate the manipulator arm 60. The arm operation unit 80 includes an enable switch 81, a joystick 82, and a switch unit 83. The enable switch 81 enables or disables movement of the manipulator arm 60 in response to the joystick 82 and the switch unit 83. The enable switch 81 enables movement of the surgical instrument 4 by the manipulator arm 60 when the enable switch 81 is pressed by an operator such as a nurse or an assistant grasping the arm operation unit 80.

The switch unit 83 includes a switch 83a to move the surgical instrument 4 in the direction in which the surgical instrument 4 is inserted into the patient P, along the longitudinal direction of the surgical instrument 4, and a switch 83b to move the surgical instrument 4 in a direction opposite to the direction in which the surgical instrument 4 is inserted into the patient P. Both the switch 83a and the switch 83b are push-button switches.

Figure 10:
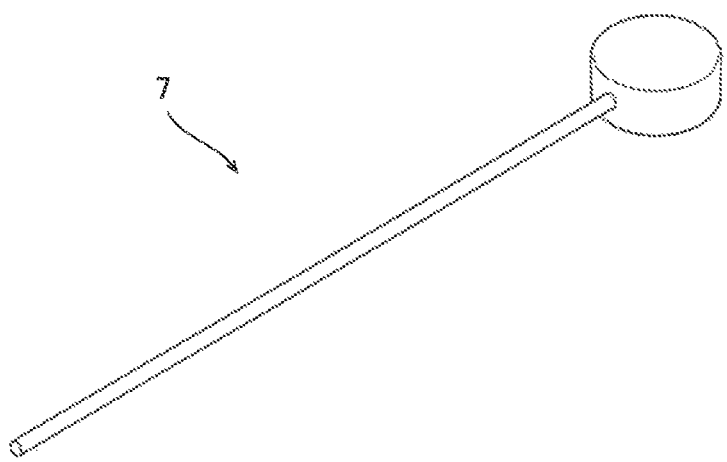
FIG. 10 is a diagram showing a pivot position setting instrument.
Figure 12:
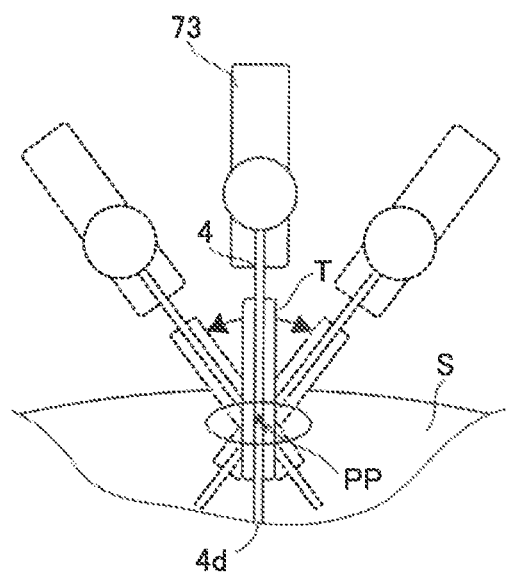
FIG. 12 is a diagram for illustrating rotation of the manipulator arm.

As shown in FIG. 8, the arm operation unit 80 includes a pivot button 85 to set a pivot position PP that serves as a fulcrum shown in FIG. 12 for movement of the surgical instrument 4 attached to the manipulator arm 60. The pivot button 85 is provided adjacent to the enable switch 81 on a surface 80b of the arm operation unit 80. The pivot button 85 is pressed when the tip end of the endoscope 6 shown in FIG. 9 or a pivot position setting instrument 7 shown in FIG. 10 is located at a position corresponding to the insertion position of a trocar T inserted into the body surface S of the patient P such that the pivot position PP is set and stored in the storage 32. In the setting of the pivot position PP, the pivot position PP is set as one point, and the direction of the surgical instrument 4 is not set.

As shown in FIG. 1, the endoscope 6 is attached to one (manipulator arm 60c, for example) of the plurality of manipulator arms 60, and the surgical instruments 4 other than the endoscope 6 are attached to the remaining manipulator arms 60a, 60b, and 60d, for example. Specifically, in surgery, the endoscope 6 is attached to one of four manipulator arms 60, and the surgical instruments 4 such as pairs of forceps other than the endoscope 6 are attached to the three manipulator arms 60. The pivot position PP is set with the endoscope 6 attached to the manipulator arm 60 to which the endoscope 6 is to be attached. Furthermore, pivot positions PP are set with pivot position setting instruments 7 attached to the manipulator arms 60 to which the surgical instruments 4 other than the endoscope 6 are to be attached. The endoscope 6 is attached to one of two manipulator arms 60b and 60c arranged in the center among the four manipulator arms 60 arranged adjacent to each other. That is, the pivot position PP is individually set for each of the plurality of manipulator arms 60.

As shown in FIG. 8, an adjustment button 86 for optimizing the position of the manipulator arm 60 is provided on the surface 80b of the arm operation unit 80. After the pivot position PP for the manipulator arm 60 to which the endoscope 6 has been attached is set, the adjustment button 86 is pressed such that the positions of the other manipulator arms 60 and the arm base 50 are optimized.

Figure 11:
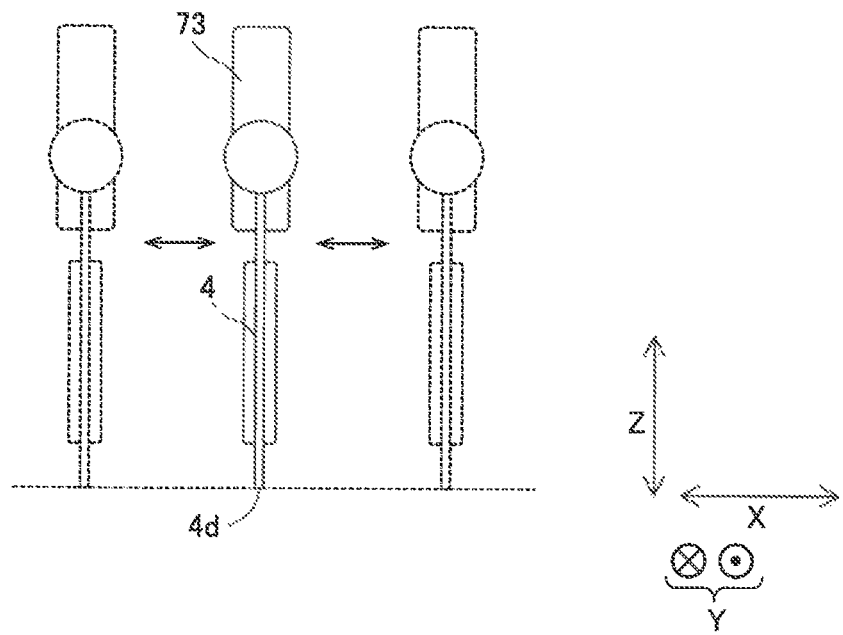
FIG. 11 is a diagram for illustrating translation of the manipulator arm.

As shown in FIG. 8, the arm operation unit 80 includes a mode switching button 84 to switch between a mode for translating the surgical instrument 4 attached to the manipulator arm 60 as shown in FIG. 11 and a mode for rotationally moving the surgical instrument 4 attached to the manipulator arm 60 as shown in FIG. 12. Furthermore, a mode indicator 84a is provided in the vicinity of the mode switching button 84. The mode indicator 84a indicates a switched mode. Specifically, the mode indicator 84a is turned on to indicate a rotational movement mode and is turned off to indicate a translational mode.

The mode indicator 84a also serves as a pivot position indicator that indicates that the pivot position PP has been set.

As shown in FIG. 11, in the mode for translating the manipulator arm 60, the manipulator arm 60 is moved such that the tip end 4d of the surgical instrument 4 moves on an X-Y plane. As shown in FIG. 12, in the mode for rotationally moving the manipulator arm 60, when the pivot position PP is not set, the manipulator arm 60 is moved such that the surgical instrument 4 rotationally moves about the pair of forceps 4b, and when the pivot position PP is set, the manipulator arm 60 is moved such that the surgical instrument 4 rotationally moves about the pivot position PP as a fulcrum. The surgical instrument 4 is rotationally moved while the shaft 4c of the surgical instrument 4 is inserted into the trocar T.

As shown in FIG. 13, the manipulator arm 60 includes a plurality of servomotors M1, encoders E1, and speed reducers so as to correspond to a plurality of joints 64 of the arm portion 61. The encoders E1 detect the rotation angles of the servomotors M1. The speed reducers slow down rotation of the servomotors M1 to increase the torques.

As shown in FIG. 13, the translation mechanism 70 includes the servomotors M2 to rotate the rotary bodies provided in the driven unit 4a of the surgical instrument 4, the servomotor M3 to translate the surgical instrument 4, encoders E2 and E3, and speed reducers. The encoders E2 and E3 detect the rotation angles of the servomotors M2 and M3, respectively. The speed reducers slow down rotation of the servomotors M2 and M3 to increase the torques.

The positioner 40 includes a plurality of servomotors M4, encoders E4, and speed reducers so as to correspond to a plurality of joints 43 of the positioner 40. The encoders E4 detect the rotation angles of the servomotors M4. The speed reducers slow down rotation of the servomotors M4 to increase the torques.

The medical cart 3 includes servomotors M5 to drive a plurality of front wheels of the medical cart 3, respectively, encoders E5, and speed reducers. The encoders E5 detect the rotation angles of the servomotors M5. The speed reducers slow down rotation of the servomotors M5 to increase the torques.

The controller 31 of the medical cart 3 includes an arm controller 31a to control movement of the plurality of manipulator arms 60 based on commands, and a positioner controller 31b to control movement of the positioner 40 and driving of the front wheels of the medical cart 3 based on commands. Servo controllers C1 that control the servomotors M1 to drive the manipulator arm 60 are electrically connected to the arm controller 31a. The encoders E1 that detect the rotation angles of the servomotors M1 are electrically connected to the servo controllers C1.

Servo controllers C2 that control the servomotors M2 to drive the surgical instrument 4 are electrically connected to the arm controller 31a. The encoders E2 that detect the rotation angles of the servomotors M2 are electrically connected to the servo controllers C2. A servo controller C3 that controls the servomotor M3 to translate the translation mechanism 70 is electrically connected to the arm controller 31a. The encoder E3 that detects the rotation angle of the servomotor M3 is electrically connected to the servo controller C3.

An operation command input to the remote control apparatus 2 is input to the arm controller 31a. The arm controller 31a generates position commands based on the input operation command and the rotation angles detected by the encoders E1 to E3, and outputs the position commands to the servo controllers C1 to C3. The servo controllers C1 to C3 generate current commands based on the position commands input from the arm controller 31a and the rotation angles detected by the encoders E1 to E3, and output the current commands to the servomotors M1 to M3. Thus, the manipulator arm 60 is moved according to the operation command input to the remote control apparatus 2.

As shown in FIG. 13, the arm controller 31a of the controller 31 operates the manipulator arm 60 based on an input signal from the joystick 82 of the arm operation unit 80. Specifically, the arm controller 31a generates position commands based on the input signal (operation command) input from the joystick 82 and the rotation angles detected by the encoders E1, and outputs the position commands to the servo controllers C1. The servo controllers C1 generate current commands based on the position commands input from the arm controller 31a and the rotation angles detected by the encoders E1, and output the current commands to the servomotors M1. Thus, the manipulator arm 60 is moved according to the operation command input to the joystick 82.

The arm controller 31a of the controller 31 operates the manipulator arm 60 based on an input signal from the switch unit 83 of the arm operation unit 80. Specifically, the arm controller 31a generates a position command based on an operation command, which is the input signal input from the switch unit 83, and the rotation angle detected by the encoders E1 or the encoder E3, and outputs the position command to the servo controllers C1 or the servo controller C3. The servo controllers C1 or the servo controller C3 generates a current command based on the position command input from the arm controller 31a and the rotation angle detected by the encoders E1 or the encoder E3, and outputs the current command to the servomotors M1 or the servomotor M3. Thus, the manipulator arm 60 is moved according to the operation command input to the switch unit 83.

As shown in FIG. 13, servo controllers C4 that control the servomotors M4 to move the positioner 40 are electrically connected to the positioner controller 31b. The encoders E4 that detect the rotation angles of the servomotors M4 are electrically connected to the servo controllers C4. Servo controllers C5 that control the servomotors M5 to drive the front wheels of the medical cart 3 are electrically connected to the positioner controller 31b. The encoders E5 that detect the rotation angles of the servomotors M5 are electrically connected to the servo controllers C5.

An operation command related to setting a preparation position, for example, is input from the input 33 to the positioner controller 31b. The positioner controller 31b generates position commands based on the operation command input from the input 33 and the rotation angles detected by the encoders E4, and outputs the position commands to the servo controllers C4. The servo controllers C4 generate current commands based on the position commands input from the positioner controller 31b and the rotation angles detected by the encoders E4, and output the current commands to the servomotors M4. Thus, the positioner 40 is moved according to the operation command input to the input 33. Similarly, the positioner controller 31b moves the medical cart 3 based on an operation command from the input 33.

Figure 14:
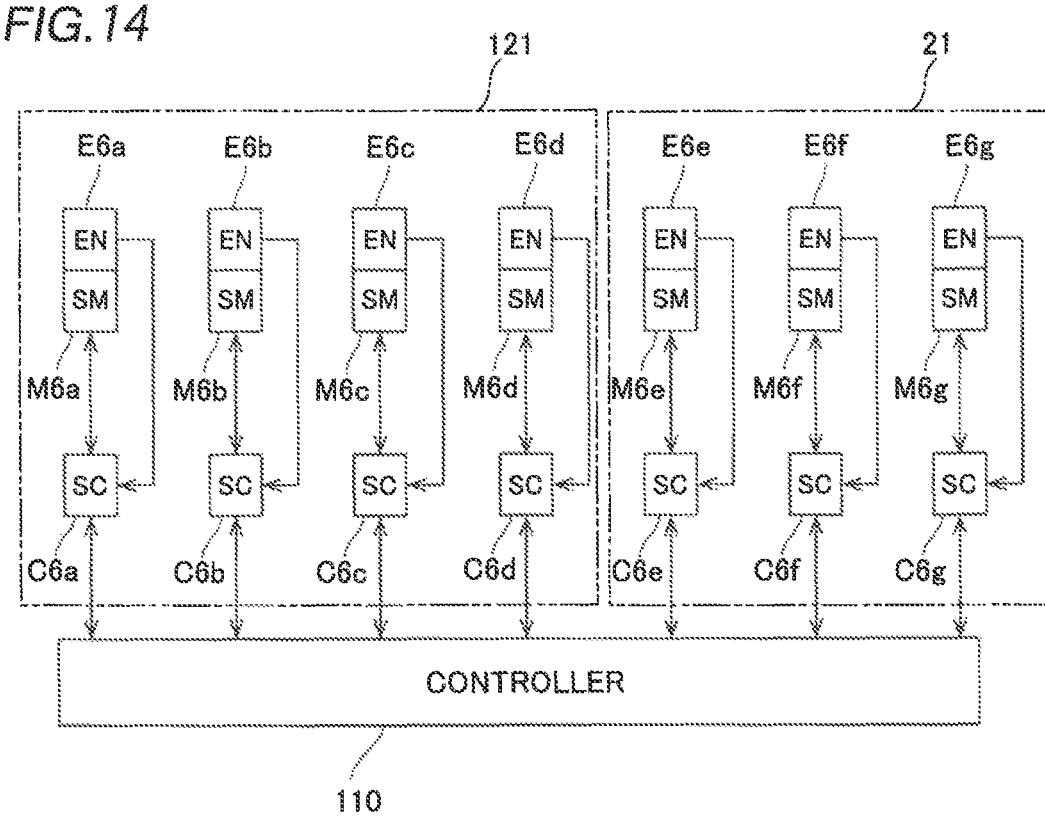
FIG. 14 is a block diagram showing the configuration of a controller of the remote control apparatus according to the first embodiment.

As shown in FIG. 14, the remote control apparatus 2 includes a controller 110. Servo controllers C6a to C6g that control servomotors M6a to M6g provided so as to correspond to the axes A1 to A7, which are the rotation axes of the operation unit 120 including the arms 121 and the operation handle 21, are electrically connected to the controller 110. Furthermore, encoders E6a to E6g that detect the rotation angles of the servomotors M6a to M6g are electrically connected to the servo controllers C6a to C6g. The servomotors M6a to M6g, the servo controllers C6a to C6g, and the encoders E6a to E6g are provided in each of the operation unit 120L and the operation unit 120R. The servomotors M6a to M6g are examples of a drive.

Figure 15:
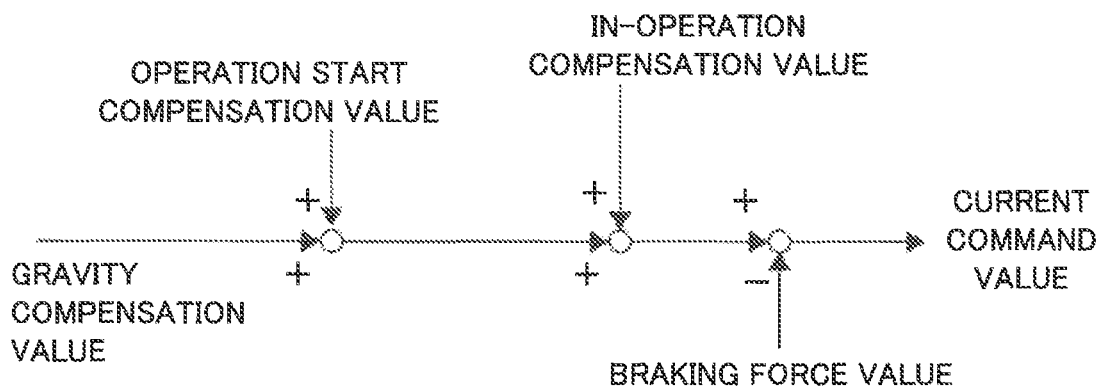
FIG. 15 is a diagram for illustrating an operation start compensation value and an in-operation compensation value added to a gravity compensation value and a braking force value subtracted from the gravity compensation value.

As shown in FIG. 15, the controller 110 controls the servomotors M6a to M6g to generate torques that cancel gravitational torques generated on the rotation axes A1 to A7 of the servomotors M6a to M6g according to the posture of the operation unit 120. Specifically, the controller 110 determines a gravity parameter $\tau_1$ for canceling a gravity torque. The controller 110 controls the servomotors M6a to M6g to exert a torque that cancels the gravity torque using a gravity compensation value based on a current command value corresponding to the determined gravity parameter $\tau_1$. Thus, the operator can operate the operation unit 120 with a relatively small force. The gravity compensation value, an operation start compensation value described below, an in-operation compensation value, and a braking force value are set for each rotation axis.

The controller 110 generates a torque on at least one of the rotation axes A1 to A7 of the servomotors M6a to M6g according to an operation on the operation unit 120, and controls at least one of the servomotors M6a to M6g to assist the operation of the operator. Specifically, in the first embodiment, the controller 110 controls at least one of the servomotors M6a to M6g to exert at least one of an operation start assisting force exerted when the operation unit 120 starts to be operated, an in-operation assisting force exerted when the operation unit 120 is being operated, or a braking force exerted when the operation unit 120 is stopped. The operation start assisting force refers to a force that assists in reducing a force required to operate the operation unit 120 at the initial stage of the movement in which the operation on the operation unit 120 is accelerated. The in-operation assisting force refers to a force that assists in reducing a force required to operate the operation unit 120 while the operation unit 120 is being operated at an operation speed $\omega$ after the operation unit 120 starts to move. The braking force refers to a force that increases a force required to operate the operation unit 120 when the operation unit 120 is stopped. In the first embodiment, the controller 110 controls at least one of the servomotors M6a to M6g to exert all of the operation start assisting force, the in-operation assisting force, and the braking force.

In the first embodiment, the controller 110 changes at least one of the level of the operation start assisting force, the level of the in-operation assisting force, or the level of the braking force based on a level changing operation of the operator. In the first embodiment, the controller 110 changes all of the level of the operation start assisting force, the level of the in-operation assisting force, and the level of the braking force based on the level changing operation of the operator. The level is changed such that the load given when the operation unit 120 is operated is changed.

Figure 16:
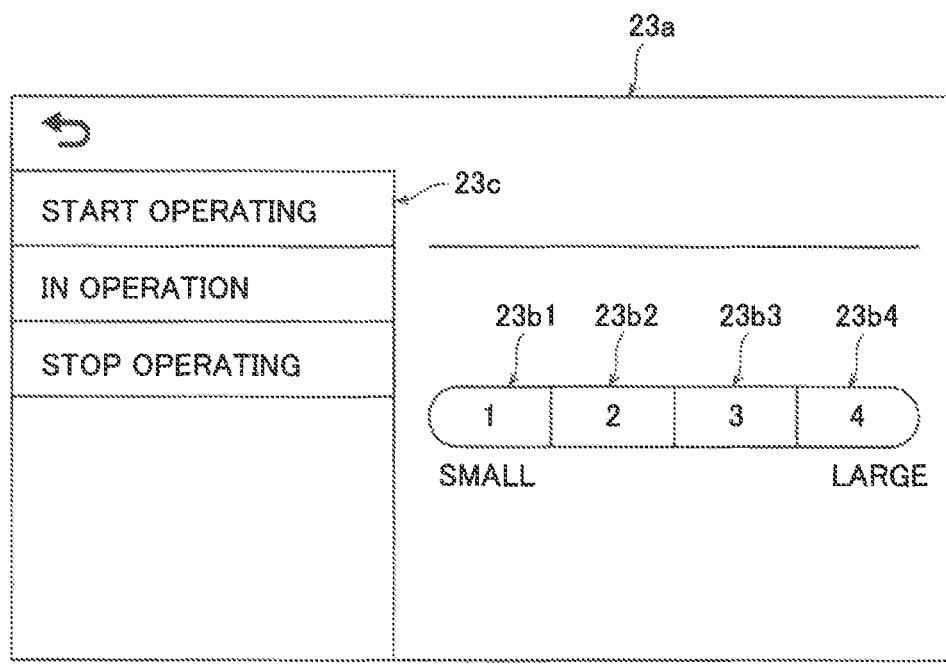
FIG. 16 is a diagram showing a level change receiver according to the first embodiment.

In the first embodiment, as shown in FIG. 16, the surgical system 100 includes a level change receiver 23a to receive a change in at least one of the level of the operation start assisting force, the level of the in-operation assisting force, or the level of the braking force. In the first embodiment, the level change receiver 23a receives changes in all of the level of the operation start assisting force, the level of the in-operation assisting force, and the level of the braking force.

In the first embodiment, at least one of the operation start assisting force, the in-operation assisting force, or the braking force has a plurality of levels. The level change receiver 23a includes level selectors 23b1 to 23b4 corresponding to the plurality of levels. In the first embodiment, the operation start assisting force, the in-operation assisting force, and the braking force each have four levels. The level selectors 23b1 to 23b4 correspond to a small level, a slightly small level, a slightly large level, and a large level, respectively.

In the first embodiment, the level change receiver 23a includes a level change target selector 23c for the operator to select a target to be changed in level from among the operation start assisting force, the in-operation assisting force, and the braking force. The level selectors 23b1 to 23b4 receive a level change for the target selected through the level change target selector 23c. For example, when a START OPERATING button of the level change target selector 23c is pressed, the level selectors 23b1 to 23b4 receive a change in the level of the operation start assisting force. When an IN OPERATION button of the level change target selector 23c is pressed, the level selectors 23b1 to 23b4 receive a change in the level of the in-operation assisting force. When a STOP OPERATING button of the level change target selector 23c is pressed, the level selectors 23b1 to 23b4 receive a change in the level of the braking force. The operation of the operator to press the level selectors 23b1 to 23b4 is hereinafter referred to as a level change operation of the operator.

In the first embodiment, the level change receiver 23a is arranged on the remote control apparatus 2. For example, the level change receiver 23a is displayed on the touch panel 23 of the remote control apparatus 2. The level selectors 23b1 to 23b4 and the level change target selector 23c are touch buttons.

Operation Start Assisting Power

Figure 17:
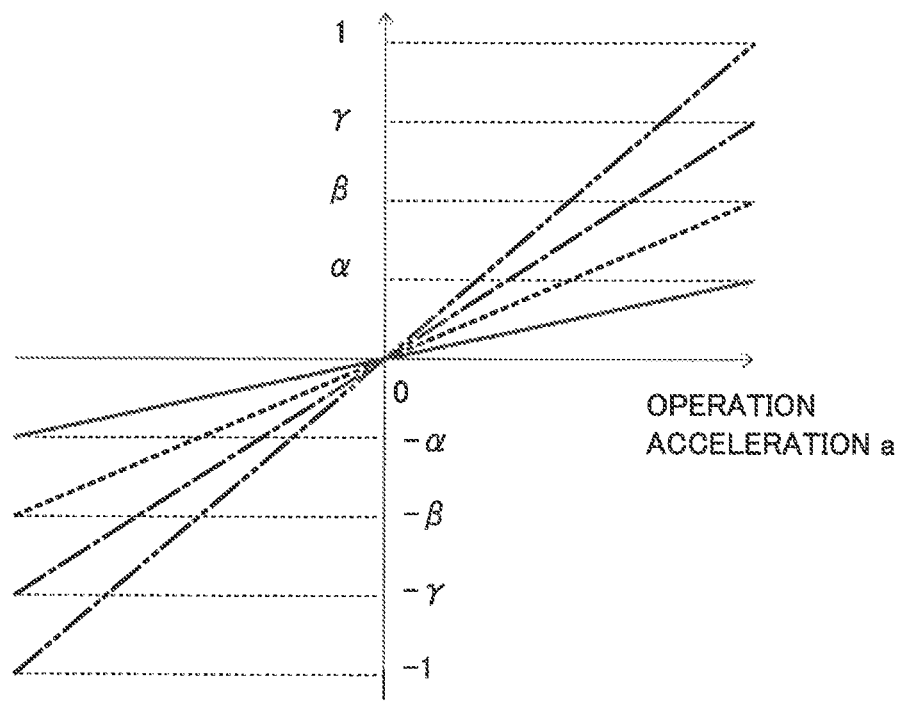
FIG. 17 is a diagram showing an operation start parameter according to the first embodiment.
Figure 18:
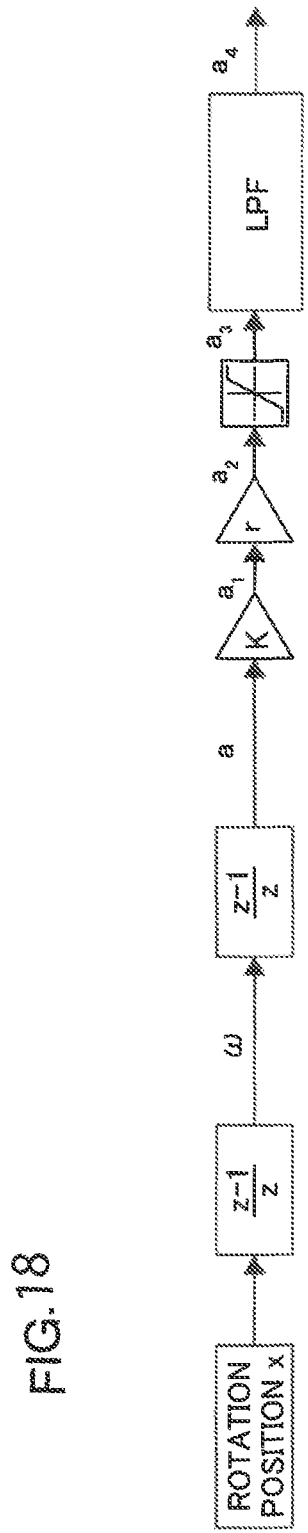
FIG. 18 is a control block diagram for generating an operation start assisting force according to the first embodiment.

In the first embodiment, as shown in FIGS. 17 and 18, the controller 110 determines the value of an operation start parameter $\tau_2$ of at least one of the servomotors M6a to M6g based on an operation acceleration a with respect to the operation unit 120. The controller 110 controls at least one of the servomotors M6a to M6g to exert the operation start assisting force using the determined value of the operation start parameter $\tau_2$. Specifically, the controller 110 exerts the operation start assisting force based on the operation start compensation value obtained by applying an LPF to a current command value corresponding to the determined operation start parameter $\tau_2$. The LPF refers to a low-pass filter. For example, the controller 110 controls the servomotors M6a, M6b, M6c, and M6e corresponding to the A1, A2, A3, and A5 axes to exert the operation start assisting force. As shown in FIG. 15, the operation start compensation value is added to the gravity compensation value. Thus, the operation start assisting force acts on the A1, A2, A3 and A5 axes. In the following description, rotation to a first side about each of the axes A1, A2, A3, and A5 is defined as rotation in a positive direction, and rotation to a second side about each of the axes A1, A2, A3, and A5 is defined as rotation in a negative direction.

In the first embodiment, as shown in FIG. 17, the controller 110 linearly increases the absolute value of the operation start parameter $T_2$ as the absolute value of the operation acceleration a increases. The controller 110 changes the level of the operation start assisting force by changing the magnitude of the operation start parameter $T_2$ with respect to the operation acceleration a based on the level change operation of the operator.

Specifically, as shown in FIG. 18, the encoders E6a, E6b, E6c, and E6e detect the rotation positions x of the servomotors M6a, M6b, M6c, and M6e, respectively. The rotation position x detected by the encoder E6a, E6b, E6c, or E6e is input to the controller 110. The controller 110 differentiates the input rotation position x to calculate the operation speed ω. The controller 110 differentiates the calculated operation speed ω to calculate the operation acceleration a. The controller 110 multiplies the calculated operation acceleration a by a gain K. The operation acceleration a having been multiplied by the gain K has been multiplied is hereinafter referred to as a gain-multiplied acceleration $a_1$.

The controller 110 multiplies the gain-multiplied acceleration $a_1$ by the multiplying factor of a level r corresponding to any of the level selectors 23b1 to 23b4 pressed by the operator. For example, when the level selector 23b1 is pressed, the gain-multiplied acceleration $a_1$ is multiplied by a multiplying factor α. When the level selector 23b2 is pressed, the gain-multiplied acceleration $a_1$ is multiplied by a multiplying factor β. When the level selector 23b3 is pressed, the gain-multiplied acceleration $a_1$ is multiplied by a multiplying factor γ. When the level selector 23b4 is pressed, the gain-multiplied acceleration $a_1$ is multiplied by a multiplying factor 1. It should be noted that α, β, γ, and 1 have a relationship of $0 \leq \alpha \leq \beta < \gamma < 1$. The gain-multiplied acceleration $a_1$ having been multiplied by the multiplying factor is hereinafter referred to as a multiplying factor-multiplied acceleration $a_2$.

The controller 110 limits the multiplying factor-multiplied acceleration $a_2$ between the upper limit value and the lower limit value. Thus, action of an excessive operation start assisting force is significantly reduced or prevented. For example, the operation unit 120 may be hit or the operation units 120 may come into contact with each other. In this case, the operation start assisting force becomes excessively large. The multiplying factor-multiplied acceleration $a_2$ is limited between the upper limit value and the lower limit value such that excessive movement of the operation unit 120 can be significantly reduced or prevented. The multiplying factor-multiplied acceleration $a_2$ limited between the upper limit value and the lower limit value is hereinafter referred to as a limited acceleration $a_3$.

The controller 110 applies the LPF to the limited acceleration $a_3$. Thus, high-frequency noise can be removed from the limited acceleration $a_3$. In particular, the limited acceleration $a_3$ is calculated by differentiation of the speed, and thus high-frequency noise tends to be large, and the ratio of high-frequency noise to the components of the limited acceleration $a_3$ becomes large. The limited acceleration $a_3$ to which the LPF has been applied is hereinafter referred to as a post-LPF acceleration $a_4$. The controller 110 adds the post-LPF acceleration $a_4$ as the operation start compensation value to the gravity compensation value.

In FIG. 17, a two-dot chain line represents the operation start parameter $T_2$ in a case in which the level selector 23b1 is pressed. A one-dot chain line represents the operation start parameter $T_2$ in a case in which the level selector 23b2 is pressed. A dotted line represents the operation start parameter $T_2$ in a case in which the level selector 23b3 is pressed. A solid line represents the operation start parameter $T_2$ in a case in which the level selector 23b4 is pressed.

In-Operation Assisting Force

Figure 19:
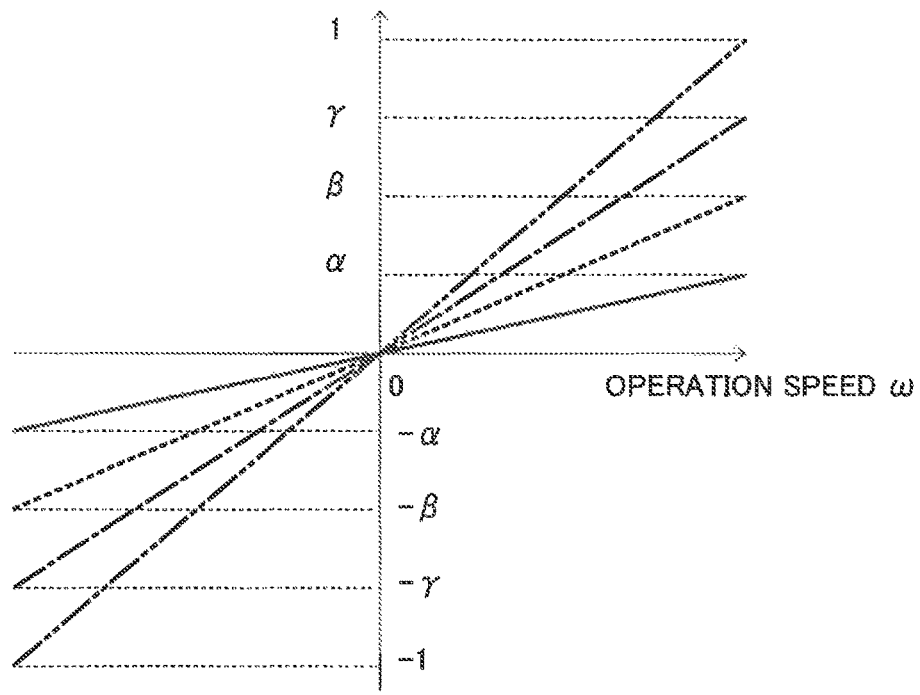
FIG. 19 is a diagram showing an in-operation parameter according to the first embodiment.

In the first embodiment, as shown in FIG. 19, the controller 110 determines the value of an in-operation parameter $\tau_3$ of at least one of the servomotors M6a to M6g based on the operation speed ω with respect to the operation unit 120. The controller 110 controls at least one of the servomotors M6a to M6g to exert the in-operation assisting force using the determined value of the in-operation parameter $T_3$. Specifically, the controller 110 exerts the in-operation assisting force based on the in-operation compensation value obtained by applying the LPF to a current command value corresponding to the determined in-operation parameter $T_3$. For example, the controller 110 controls the servomotors M6e and M6f corresponding to the A5 and A6 axes to exert the in-operation assisting force. As shown in FIG. 15, the in-operation compensation value is added to the gravity compensation value. Thus, the in-operation assisting force acts on the A5 and A6 axes. In the following description, rotation to a first side about each of the A5 and A6 axes is defined as rotation in a position direction, and rotation to a second side about each of the A5 and A6 axes is defined as rotation in a negative direction.

In the first embodiment, as shown in FIG. 19, the controller 110 linearly increases the absolute value of the in-operation parameter $T_3$ as the absolute value of the operation speed ω increases. The controller 110 changes the level of the in-operation assisting force by changing the magnitude of the in-operation parameter $T_3$ based on the level change operation of the operator.

Figure 20:
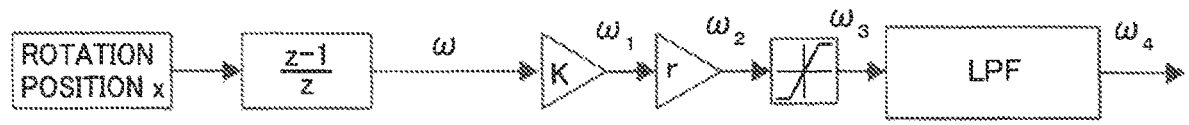
FIG. 20 is a control block diagram for generating an in-operation assisting force according to the first embodiment.

Specifically, as shown in FIG. 20, the encoders E6e and E6f detect the rotation positions x of the servomotors M6e and M6f, respectively. The rotation position x detected by the encoder E6e or E6f is input to the controller 110. The controller 110 differentiates the input rotation position x to calculate the operation speed ω. The controller 110 multiplies the calculated speed by a gain K. The operation speed ω having been multiplied by the gain K is hereinafter referred to as a gain-multiplied speed $\omega_1$.

The controller 110 multiplies the gain-multiplied speed $\omega_1$ by the multiplying factor of the level r corresponding to any of the level selectors 23b1 to 23b4 pressed by the operator. For example, when the level selector 23b1 is pressed, the gain-multiplied speed $\omega_1$ is multiplied by the multiplying factor α. When the level selector 23b2 is pressed, the gain-multiplied speed $\omega_1$ is multiplied by the multiplying factor β. When the level selector 23b3 is pressed, the gain-multiplied speed $\omega_1$ is multiplied by the multiplying factor γ. When the level selector 23b is pressed, the gain-multiplied speed $\omega_1$ is multiplied by the multiplying factor 1. It should be noted that α, β, γ, and 1 have a relationship of $0 \leq \alpha < \beta < \gamma < 1$. The gain-multiplied speed $\omega_1$ multiplied by the multiplying factor is hereinafter referred to as a multiplying factor-multiplied speed $\omega_2$.

The controller 110 limits the multiplying factor-multiplied speed $\omega_2$ between the upper limit value and the lower limit value. Thus, when the operation unit 120 is operated at a speed at which the operation unit 120 is not moved in normal operation, the multiplying factor-multiplied speed $\omega_2$ is limited, and thus an excessive increase in the in-operation assisting force is significantly reduced or prevented. The multiplying factor-multiplied speed $\omega_2$ limited between the upper limit value and the lower limit value is hereinafter referred to as a limited speed $\omega_3$.

The controller 110 applies the LPF to the limited speed $\omega_3$. The limited speed $\omega_3$ to which the LPF has been applied is hereinafter referred to as a post-LPF speed $\omega_4$. The controller 110 adds the post-LPF speed $\omega_4$ as the in-operation compensation value to the gravity compensation value.

In FIG. 19, a two-dot chain line represents the in-operation parameter $\tau_3$ in a case in which the level selector 23b1 is pressed. A one-dot chain line represents the in-operation parameter $\tau_3$ in a case in which the level selector 23b2 is pressed. A dotted line represents the in-operation parameter $\tau_3$ in a case in which the level selector 23b3 is pressed. A solid line represents the in-operation parameter $\tau_3$ in a case in which the level selector 23b4 is pressed.

Braking Force

Figure 23:
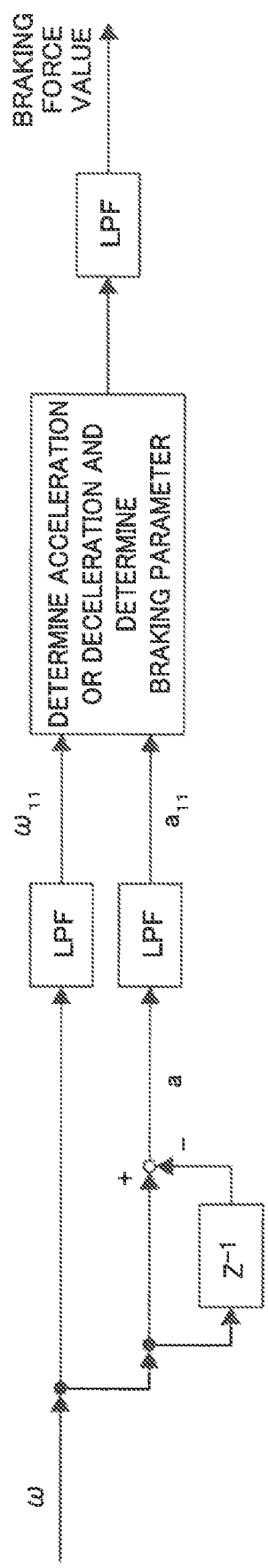
FIG. 23 is a control block diagram for generating a braking force according to the first embodiment.

As shown in FIGS. 21 to 23, the controller 110 determines the value of a braking parameter $\tau$ of at least one of the servomotors M6a to M6g based on the operation acceleration a and the operation speed $\omega$ with respect to the operation unit 120. The controller 110 controls at least one of the servomotors M6a to M6g to exert the braking force using the determined value of the braking parameter $\tau$. The braking force acts when the operation unit 120 is stopped. Specifically, the controller 110 exerts the braking force based on the braking force value obtained by applying the LPF to a current command value corresponding to the determined braking parameter $\tau$. For example, the controller 110 controls the servomotors M6a, M6b, and M6c corresponding to the A1, A2, and A3 axes to exert the braking force. The servomotors M6a, M6b, and M6c correspond to operations for moving the manipulator arm 60 three-dimensionally. The controller 110 may perform a control to exert the braking force on an axis other than the A1, A2, and A3 axes. For example, the controller 110 controls the servomotor M6g corresponding to the A7 axis to exert the braking force. The servomotor M6g corresponds to an operation for rotating the pair of forceps 4b about an axis along the shaft 4c.

Specifically, as shown in FIG. 23, the encoders E6a, E6b, and E6c detect the rotation positions x of the servomotors M6a, M6b, and M6c, respectively. The rotation position x detected by the encoder E6a, E6b, or E6c is input to the controller 110. The controller 110 differentiates the input rotation position x to calculate the operation speed $\omega$. The operation speed $\omega$ refers to a rotation speed about the A1, A2, or A3 axis. The controller 110 applies the LPF to the input operation speed $\omega$. The operation speed $\omega$ to which the LPF has been applied is hereinafter referred to as a post-LPF speed $\omega_{11}$. Furthermore, the controller 110 calculates the operation acceleration a by differentiation of the input operation speed $\omega$ and applies the LPF to the calculated operation acceleration a. The operation acceleration a to which the LPF has been applied is hereinafter referred to as a post-LPF acceleration $a_{11}$. The controller 110 determines whether the operation unit 120 is accelerated or decelerated based on the post-LPF speed $\omega_{11}$ and the post-LPF acceleration $a_{11}$. The controller 110 determines the braking parameter $\tau$ based on the determination of acceleration or deceleration. The controller 110 applies the LPF to the braking parameter $\tau$. The braking force value to which the LPF has been applied is subtracted from the gravity compensation value. Thus, the braking force acts on the A1, A2, or A3 axis.

The controller 110 controls the servomotors M6a, M6b, and M6c to exert the braking force when an operation on the operation unit 120 is decelerated and/or accelerated. Specifically, as shown in FIG. 21, the controller 110 controls the servomotors M6a, M6b, and M6c to exert the braking force when the operation on the operation unit 120 is accelerated. That is, the controller 110 exerts the braking force by software during acceleration.

In the first embodiment, as shown in FIG. 21, when the operation is accelerated, the controller 110 increases the absolute value of the braking parameter $\tau$ as the absolute value of the operation speed $\omega$ increases when the absolute value of the operation speed $\omega$ is less than a first acceleration threshold. The controller 110 maintains the braking parameter $\tau$ constant when the absolute value of the operation speed $\omega$ is equal to or greater than the first acceleration threshold and is less than a second acceleration threshold. The controller 110 decreases the absolute value of the braking parameter $\tau$ as the absolute value of the operation speed $\omega$ increases when the absolute value of the operation speed $\omega$ is equal to or greater than the second acceleration threshold and is less than a third acceleration threshold. The controller 110 sets the braking parameter $\tau$ to zero when the absolute value of the operation speed $\omega$ is equal to or greater than the third acceleration threshold.

Specifically, when the operation is accelerated, the controller 110 increases the braking parameter $\tau$ as the operation speed $\omega$ increases when the operation speed $\omega$ is less than a threshold $\omega_{a1}$, sets the braking parameter $\tau$ to constant $T_a$ when the operation speed $\omega$ is equal to or greater than the threshold $\omega_{a1}$ and is less than a threshold $\omega_{a2}$, decreases the braking parameter $\tau$ as the operation speed $\omega$ increases when the operation speed $\omega$ is equal to or greater than the threshold $C_{Ua2}$ and is less than a threshold $\omega_{a3}$, and sets the braking parameter $\tau$ to zero when the operation speed $\omega$ is equal to or greater than the threshold $\omega_{a3}$. When the operation is accelerated, the controller 110 increases the braking parameter $\tau$ as the operation speed $\omega$ increases when the operation speed $\omega$ is greater than a threshold $-\omega_{a1}$, sets the braking parameter $\tau$ to constant $-\tau_a$ when the operation speed $\omega$ is equal to or greater than a threshold $-\omega_{a2}$ and is less than the threshold $-\omega_{a1}$, decreases the braking parameter $\tau$ as the operation speed $\omega$ increases when the operation speed $\omega$ is equal to or greater than a threshold $-\omega_{a3}$ and is less than the threshold $-\omega_{a2}$, and sets the braking parameter $\tau$ to zero when the operation speed $\omega$ is equal to or less than the threshold $-\omega_{a3}$. The threshold $\omega_{a1}$ and the threshold $-\omega_{a1}$ are examples of a first acceleration threshold. The threshold $\omega_{a2}$ and the threshold $-\omega_{a2}$ are examples of a second acceleration threshold. The threshold $\omega_{a3}$ and the threshold $-\omega_{a3}$ are examples of a third acceleration threshold.

The negative operation speed $\omega$ indicates that the servomotor rotates in a reverse direction.

When the operation speed $\omega$ is between the threshold $-\omega_{a1}$ and the threshold $\omega_{a1}$, the braking parameter $\tau$ increases linearly. When the operation speed $\omega$ is between the threshold $\omega_{a2}$ and the threshold $\omega_{a3}$, the braking parameter $\tau$ decreases linearly. When the operation speed $\omega$ is between the threshold $-\omega_{a2}$ and the threshold $-\omega_{a3}$, the braking parameter τ increases linearly. When the operation speed ω is 0, the braking parameter τ is 0.

In the first embodiment, as shown in FIG. 21, the controller 110 changes the level of the braking force by changing the upper limit of the absolute value of the braking parameter τ based on the level change operation of the operator. Specifically, the controller 110 changes the upper limit of the absolute value of the braking parameter τ by changing the threshold $\omega_{a1}$, the threshold $\omega_{a2}$, the threshold $-\omega_{a1}$, and the threshold $-\omega_{a2}$. For example, the threshold $\omega_{a1}$, the threshold $\omega_{a2}$, the threshold $-\omega_{a1}$, and the threshold $-\omega_{a2}$ are changed to a threshold $\omega_{a11}$, a threshold $\omega_{a12}$, a threshold $-\omega_{a11}$, and a threshold $-\omega_{a12}$, respectively, such that the maximum of the absolute value of the braking parameter τ is increased from $\tau_a$ to $\alpha\tau_a$. The maximum of the absolute value of the braking parameter τ is changed to any of $\tau_a$, $\alpha\tau_a$, $\beta\tau_a$, and $\gamma\tau_a$. It should be noted that α, β, and γ have a relationship of $1<\alpha<\beta<\gamma$. The maximums of the absolute values of the braking parameters τ, which are $\gamma\tau_a$, $\beta\tau_a$, $\alpha\tau_a$, and $\tau_a$, correspond to the level selectors 23b4, 23b3, 23b2, and 23b1, respectively.

Even when the maximum value of the braking parameter τ is changed, the slope of the braking parameter τ is not changed. The slope is the rate of increase of the braking parameter τ with respect to the rate of increase of the operation speed ω in a case in which the operation speed ω is between 0 and the threshold $\omega_{a1}$, for example.

In FIG. 21, a solid line represents the braking parameter τ in a case in which the level selector 23b1 is pressed. A dotted line represents the braking parameter τ in a case in which the level selector 23b2 is pressed. A one-dot chain line represents the braking parameter τ in a case in which the level selector 23b3 is pressed. A two-dot chain line represents the braking parameter τ in a case in which the level selector 23b4 is pressed.

As shown in FIG. 22, the controller 110 controls the servomotors M6a, M6b, and M6c to exert the braking force when the operation on the operation unit 120 is decelerated. That is, the controller 110 exerts the braking force by software during deceleration.

In the first embodiment, when the operation is decelerated, the controller 110 maintains the braking parameter τ constant when the absolute value of the operation speed ω is greater than a deceleration threshold. The controller 110 decreases the absolute value of the braking parameter τ as the absolute value of the operation speed ω decreases when the absolute value of the operation speed ω is equal to or less than the deceleration threshold.

Specifically, when the operation is decelerated, the controller 110 sets the braking parameter τ to constant $\tau_b$ when the operation speed ω is greater than a threshold $\omega_b$, and decreases the braking parameter τ as the operation speed ω decreases when the operation speed ω is equal to or less than the threshold $\omega_b$. When the operation is decelerated, the controller 110 sets the braking parameter τ to constant $-\tau_b$ when the operation speed ω is less than a threshold $-\omega_b$, and increases the braking parameter τ as the operation speed ω increases when the operation speed ω is equal to or greater than the threshold $-\omega_b$. The threshold $\omega_b$ and the threshold $-\omega_b$ are examples of a deceleration threshold.

More specifically, when the operation speed ω is between the threshold $\omega_b$ and 0, the braking parameter τ decreases linearly. When the operation speed ω is between the threshold $-\omega_b$ and 0, the braking parameter τ increases linearly. When the operation speed ω is 0, the braking parameter τ is 0.

In the first embodiment, the controller 110 changes the level of the braking force by changing the upper limit of the absolute value of the braking parameter τ based on the level change operation of the operator. Specifically, the controller 110 changes the upper limit of the absolute value of the braking parameter τ by changing the threshold $\omega_b$ and the threshold $-\omega_b$. For example, the threshold $\omega_b$ and the threshold $-\omega_b$ are changed to a threshold $\omega_{b1}$ and a threshold $-\omega_{b1}$, respectively, such that the maximum value of the braking parameter τ is increased from $\tau_b$ to $\alpha\tau_b$. The maximum of the absolute value of the braking parameter τ is changed to any of $\tau_b$, $\alpha\tau_b$, $\beta\tau_b$, and $\gamma\tau_b$. It should be noted that α, β, and γ have a relationship of $1<\alpha<\beta<\gamma$. The maximums of the absolute values of the braking parameters τ, which are $\gamma\tau_b$, $\beta\tau_b$, $\alpha\tau_b$, $\tau_b$, correspond to the level selectors 23b4, 23b3, 23b2, and 23b1, respectively.

Even when the maximum value of the braking parameter τ is changed, the slope of the braking parameter τ is not changed. The slope is the rate of increase of the braking parameter τ with respect to the rate of increase of the operation speed ω in a case in which the operation speed ω is between 0 and the threshold $\omega_b$, for example.

In FIG. 22, a solid line represents the braking parameter τ in a case in which the level selector 23b1 is pressed. A dotted line represents the braking parameter τ in a case in which the level selector 23b2 is pressed. A one-dot chain line represents the braking parameter τ in a case in which the level selector 23b3 is pressed. A two-dot chain line represents the braking parameter τ in a case in which the level selector 23b4 is pressed.

Figure 24:
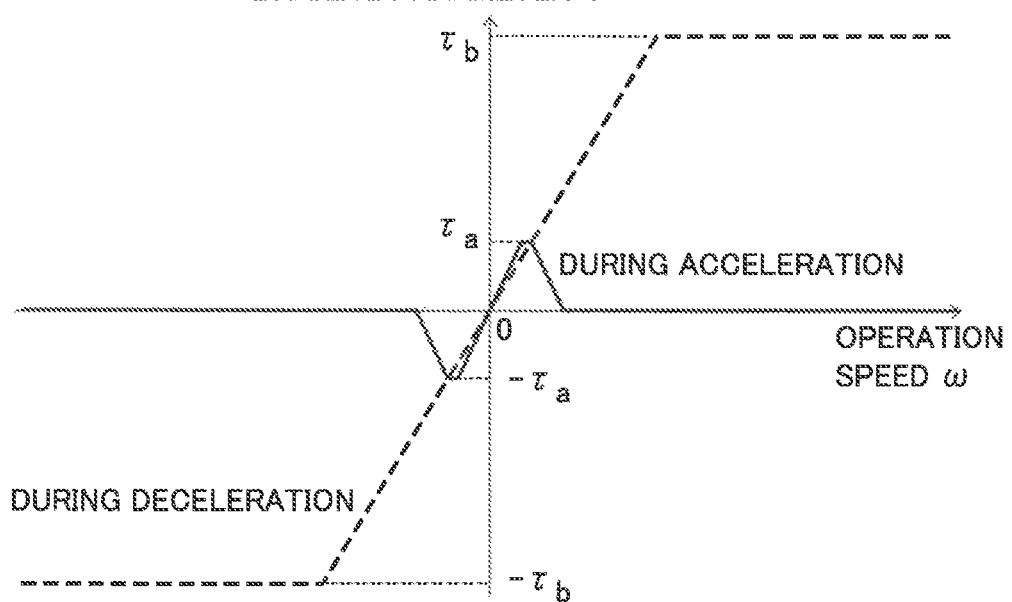
FIG. 24 is a diagram showing a braking parameter during acceleration and deceleration according to the first embodiment.

As shown in FIG. 24, the controller 110 increases the maximum $\tau_b$ of the absolute value of the braking parameter τ during deceleration of the operation to greater than the maximum $T_a$ of the absolute value of the braking parameter τ during acceleration of the operation. For example, in the first embodiment, the maximum $\tau_b$ of the braking parameter τ during deceleration of the operation shown by a dotted line is four times the maximum $T_a$ of the braking parameter τ during acceleration of the operation shown by a solid line.

As shown in FIG. 1, a storage 111 is provided to store the operation start parameter $\tau_2$, the in-operation parameter $\tau_3$, and the braking parameter τ. The storage 111 is provided in the remote control apparatus 2, for example. The storage 111 stores a table in which the operation acceleration a and the operation start parameter $\tau_2$ are associated with each other. The storage 111 stores a table in which the operation speed ω and both the in-operation parameter $\tau_3$ and the braking parameter τ are associated with each other. The controller 110 determines the operation start parameter $\tau_2$, the in-operation parameter $\tau_3$, and the braking parameter τ based on the tables.

Figure 25:
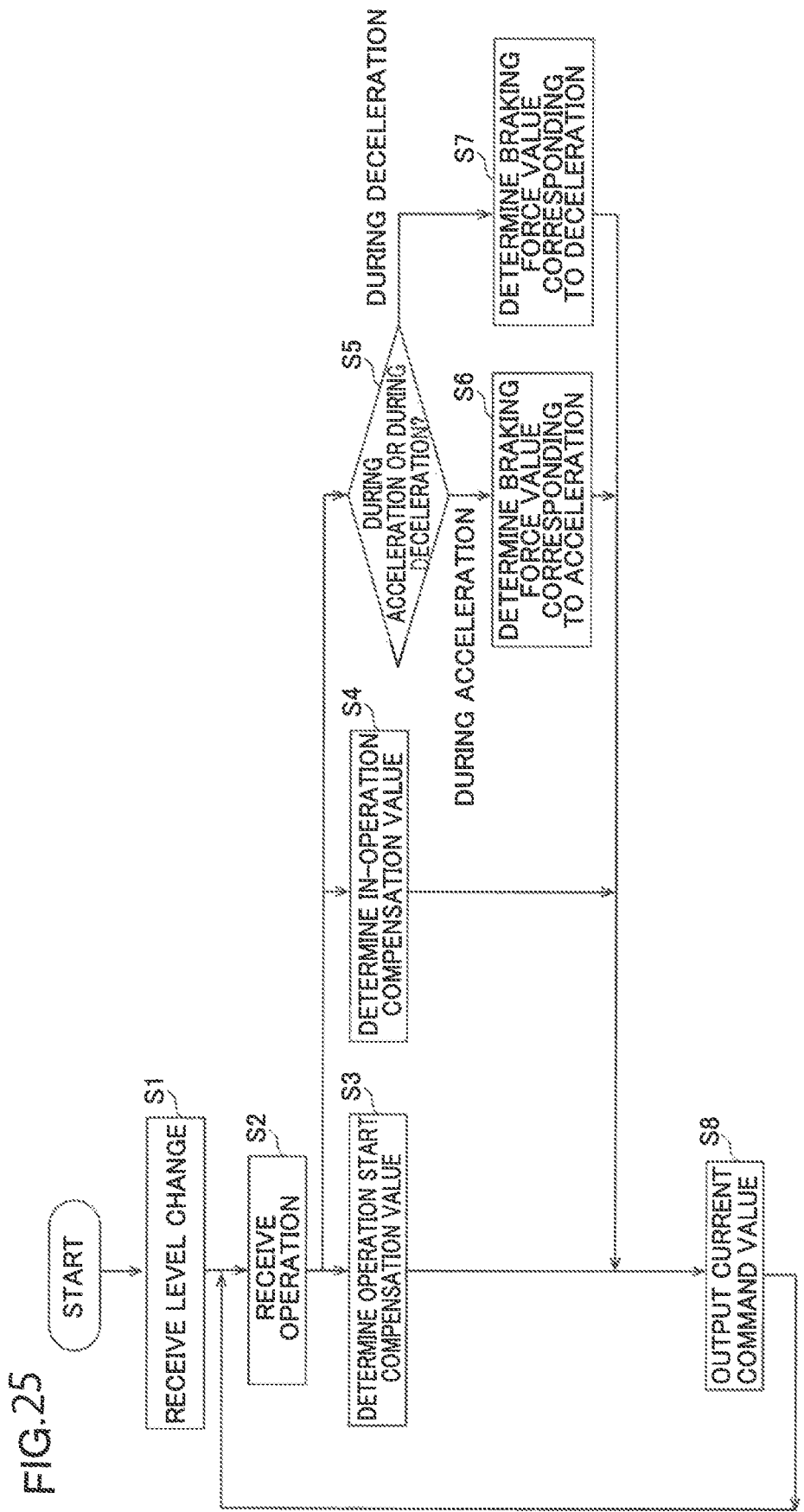
FIG. 25 is a diagram showing a control flow of the remote control apparatus according to the first embodiment.

A control flow of the surgical system 100 is now described with reference to FIG. 25.

Figure 26:
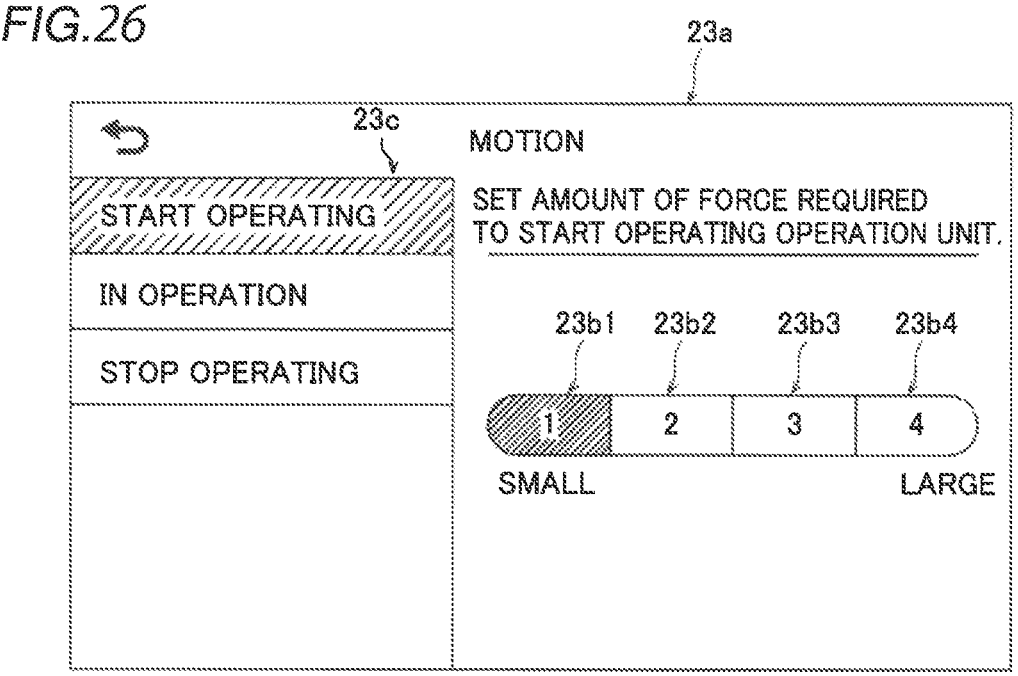
FIG. 26 is a diagram showing the level change receiver at the time of changing the level of the operation start assisting force.
Figure 27:
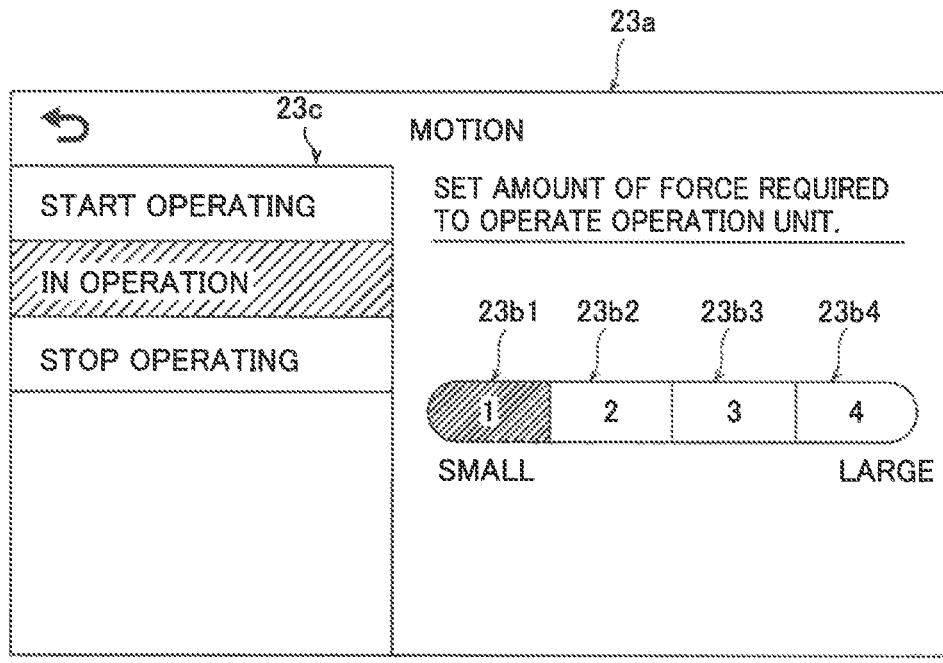
FIG. 27 is a diagram showing the level change receiver at the time of changing the level of the in-operation assisting force.
Figure 28:
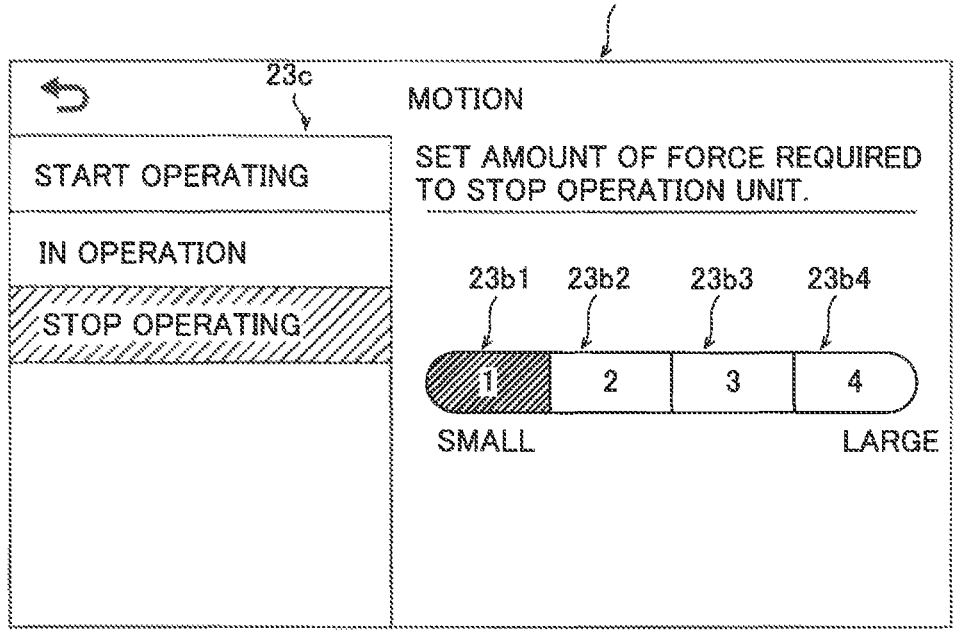
FIG. 28 is a diagram showing the level change receiver at the time of changing the level of the braking force.

In step S1, at least one of a change in the level of the operation start assisting force, a change in the level of the in-operation assisting force, or a change in the level of the braking force is received. In the first embodiment, all of a change in the level of the operation start assisting force, a change in the level of the in-operation assisting force, and a change in the level of the braking force are received. As shown in FIG. 26, when the START OPERATING button of the level change target selector 23c is pressed and any of the level selectors 23b1 to 23b4 is pressed, the change in the level of the operation start assisting force is received. As shown in FIG. 27, when the IN OPERATION button of the level change target selector 23c is pressed and any of the level selectors 23b1 to 23b4 is pressed, the change in the level of the in-operation assisting force is received. As shown in FIG. 28, when the STOP OPERATING button of the level change target selector 23c is pressed and any of the level selectors 23b1 to 23b4 is pressed, the change in the level of the braking force is received. A force to be changed in level is displayed above the level selectors 23b1 to 23b4.

In step S2, an operation on the operation unit 120 is received. Thus, the rotation positions x of the servomotors M6a to M6g of the operation unit 120 are input to the controller 110.

In step S3, the controller 110 calculates the operation acceleration a based on the rotation positions x. The controller 110 determines the value of the operation start parameter $\tau_2$ corresponding to the changed level based on the operation acceleration a. The controller 110 determines the operation start compensation value based on the determined operation start parameter $\tau_2$.

In step S4, the controller 110 calculates the operation speed $\omega$ based on the rotation positions x. The controller 110 determines the value of the in-operation parameter $\tau_3$ corresponding to the changed level based on the operation speed $\omega$. The controller 110 determines the in-operation compensation value based on the determined in-operation parameter $\tau_3$.

In step S5, the controller 110 calculates the operation speed $\omega$ and the operation acceleration a based on the rotation positions x. The controller 110 determines whether the current operation corresponds to acceleration or deceleration based on the operation speed $\omega$ and the operation acceleration a. Specifically, when the operation speed $\omega$ is positive and the acceleration is positive, the controller 110 determines that the current operation corresponds to acceleration. When the operation speed $\omega$ is positive and the acceleration is 0, the controller 110 determines that the current operation corresponds to acceleration. The operation acceleration a of 0 indicates a constant speed. When the operation speed $\omega$ is positive and the acceleration is negative, the controller 110 determines that the current operation corresponds to deceleration. When the operation speed $\omega$ is 0 and the operation acceleration a is positive, the controller 110 determines that the current operation corresponds to acceleration. When the operation speed $\omega$ is 0 and the operation acceleration a is 0, the controller 110 determines that the current operation corresponds to acceleration. When the operation speed $\omega$ is 0 and the operation acceleration a is negative, the controller 110 determines that the current operation corresponds to deceleration. When the operation speed $\omega$ is negative and the operation acceleration a is positive, the controller 110 determines that the current operation corresponds to deceleration. When the operation speed $\omega$ is negative and the operation acceleration a is 0, the controller 110 determines that the current operation corresponds to deceleration. When the operation speed $\omega$ is negative and the operation acceleration a is negative, the controller 110 determines that the current operation corresponds to acceleration.

When determining in step S5 that the current operation corresponds to acceleration, the controller 110 advances to step S6. In step S6, the controller 110 determines the braking parameter $\tau$ corresponding to the changed level. The controller 110 determines the braking force value based on the determined braking parameter $\tau$. Then, the controller 110 advances to step S8.

When determining in step S5 that the current operation corresponds to deceleration, the controller 110 advances to step S7. In step S7, the controller 110 determines the braking parameter $\tau$ corresponding to the changed level. The controller 110 determines the braking force value based on the determined braking parameter $\tau$. Then, the controller 110 advances to step S8.

In step S8, the controller 110 outputs a current command value to exert at least one of the operation start assisting force, the in-operation assisting force, or the braking force corresponding to the changed level. In the first embodiment, the controller 110 exerts all of the operation start assisting force, the in-operation assisting force, and the braking force. The operations in step S2 to step S8 described above are performed in each control cycle of the controller 110, for example.

The braking force acting when the operator tries to stop the operation unit 120 is now described.

First, when the operator tries to stop the operation unit 120, the operation speed $\omega$ is decreased. In this case, the braking force during deceleration acts on the operation unit 120. When the operation speed $\omega$ becomes equal to or less than the threshold $\omega_b$, the braking force decreases as the operation speed $\omega$ decreases. Then, the operation unit 120 is stopped. In this manner, the braking force acts during deceleration, and thus overshoot caused by the inertia of the operation unit 120 when the operator tries to stop the operation unit 120 suddenly is significantly reduced or prevented.

Even when the operator tries to make their hand operating the operation unit 120 stationary, their hand may move unintentionally. For example, their hand may move unintentionally due to spasms of the operator's hand muscles or the operator's breathing. When the operation unit 120 advances beyond a position at which the operator tries to stop the operation unit 120 due to inertia, the operator may unintentionally try to return the operation unit 120 to a desired position. In such a case, the operation unit 120 is in an accelerated state. During acceleration, the braking force acts so as to increase as the operation speed $\omega$ increases such that it is possible to significantly reduce or prevent unintentional movement of the operation unit 120 as described above.

The relationship between the operation start assisting force and the braking force is now described. The operation start assisting force depends on the acceleration, and the braking force depends on the speed. Therefore, in an operation start region, i.e., a region in which the operation unit 120 is accelerating but the speed is near zero, the braking force is small, and the influence of the operation start assisting force is large. However, as the speed increases, the braking force increases to some extent, and thus the braking force influences the operation start assisting force. On the other hand, during deceleration, the influence of the braking force is increased by setting a dead zone described below to reduce the operation start assisting force.

Advantages of First Embodiment

According to the first embodiment, the following advantages are achieved.

According to the first embodiment, as described above, the controller 110 is configured or programmed to change at least one of the level of the operation start assisting force, the level of the in-operation assisting force, or the level of the braking force based on the level change operation of the operator. Accordingly, the operator can change at least one of the level of the operation start assisting force, the level of the in-operation assisting force, or the level of the braking force to a desired level by the level change operation.

Therefore, an operation on the operation unit 120 can be appropriately assisted according to the operator.

According to the first embodiment, as described above, the controller 110 is configured or programmed to change all of the level of the operation start assisting force, the level of the in-operation assisting force, and the level of the braking force based on the level change operation of the operator. Accordingly, as compared with a case in which only one or two of the level of the operation start assisting force, the level of the in-operation assisting force, and the level of the braking force are changed, an operation on the operation unit 120 can be more appropriately assisted according to the operator. The braking force acts when the operation unit 120 is stopped such that overshoot caused by the inertia of the operation unit 120 when the operator tries to stop the operation unit 120 suddenly is significantly reduced or prevented. The braking force acts such that movement of the operation unit 120 due to a reaction caused when the operation unit 120 is suddenly stopped, for example, is significantly reduced or prevented. Overshoot is significantly reduced or prevented, and the movement of the operation unit 120 due to a reaction, for example, is significantly reduced or prevented such that the operation unit 120 of the remote control apparatus 2 can be stopped at an appropriate position. The overshoot indicates that the operation unit 120 overshoots the appropriate stop position.

According to the first embodiment, as described above, the level change receiver 23*a* is provided to receive at least one of a change in the level of the operation start assisting force, a change in the level of the in-operation assisting force, or a change in the level of the braking force. Accordingly, the controller 110 can easily change at least one of the level of the operation start assisting force, the level of the in-operation assisting force, or the level of the braking force to a desired level based on the operation received by the level change receiver 23*a*.

According to the first embodiment, as described above, the level change receiver 23*a* includes a plurality of level selectors 23*b*1 to 23*b*4 corresponding to a plurality of levels. Accordingly, the operator can change the level by operating any of the plurality of level selectors 23*b*1 to 23*b*4.

According to the first embodiment, as described above, the plurality of level selectors 23*b*1 to 23*b*4 receive a level change for the target selected through the level change target selector 23*c*. Accordingly, the plurality of level selectors 23*b*1 to 23*b*4 are provided in common for the level of the operation start assisting force, the level of the in-operation assisting force, and the level of the braking force, and thus the configuration of the level change receiver 23*a* is simplified.

According to the first embodiment, as described above, the level change receiver 23*a* is arranged on the remote control apparatus 2. Accordingly, the level change receiver 23*a* is arranged in the vicinity of the operator who operates the remote control apparatus 2, and thus the operator can easily operate the level change receiver 23*a*.

According to the first embodiment, as described above, the controller 110 is configured or programmed to determine the values of the braking parameters $\tau$ of the servomotors M6*a*, M6*b*, and M6*c* based on the operation acceleration a and the operation speed $\omega$ with respect to the operation unit 120, and control the servomotors M6*a*, M6*b*, and M6*c* to exert the braking forces using the determined values of the braking parameters $\tau$.

Accordingly, the level of the braking force can be easily changed according to the level of the braking parameter $\tau$. According to the first embodiment, as described above, the controller 110 is configured or programmed to decrease the absolute value of the braking parameter $\tau$ as the absolute value of the operation speed $\omega$ decreases when the absolute value of the operation speed $\omega$ is equal to or less than the deceleration threshold. Accordingly, it is possible to significantly reduce a sense of discomfort in operation due to switching between positive and negative braking parameters $\tau$ when the operation speed $\omega$ is near zero. Furthermore, the controller 110 changes the level of the braking force by changing the upper limit of the absolute value of the braking parameter $\tau$ based on the level change operation of the operator. Thus, the maximum value of the braking force during deceleration can be easily changed by changing the upper limit of the absolute value of the braking parameter $\tau$ during deceleration.

According to the first embodiment, as described above, the controller 110 is configured or programmed to increase the absolute value of the braking parameter $\tau$ as the absolute value of the operation speed $\omega$ increases when the absolute value of the operation speed $\omega$ is less than the first acceleration threshold. Accordingly, it is possible to significantly reduce a sense of discomfort in operation due to switching between positive and negative braking parameters $\tau$ when the operation speed $\omega$ is near zero. Furthermore, the controller 110 changes the level of the braking force by changing the upper limit of the absolute value of the braking parameter $\tau$ based on the level change operation of the operator. Thus, the maximum value of the braking force during acceleration can be easily changed by changing the upper limit of the absolute value of the braking parameter $\tau$ during acceleration.

According to the first embodiment, as described above, the controller 110 is configured or programmed to determine the values of the operation start parameters $\tau_2$ of the servomotors M6*a*, M6*b*, M6*c*, and M6*e* based on the operation acceleration a with respect to the operation unit 120, and control the servomotors M6*a*, M6*b*, M6*c*, and M6*e* to exert the operation start assisting forces using the determined values of the operation start parameters $\tau_2$. Accordingly, using the operation start parameters $\tau_2$, the servomotors M6*a*, M6*b*, M6*c*, and M6*e* can easily exert the operation start assisting forces.

According to the first embodiment, as described above, the controller 110 is configured or programmed to linearly increase the absolute value of the operation start parameter $\tau_2$ as the absolute value of the operation acceleration a increases, and change the level of the operation start assisting force by changing the magnitude of the operation start parameter $\tau_2$ with respect to the operation acceleration a based on the level change operation of the operator. Accordingly, the magnitude of the operation start parameter $\tau_2$ is changed according to the level change operation of the operator, and thus the level of the operation start assisting force can be changed using the operation start parameter $\tau_2$ that has been changed in magnitude.

According to the first embodiment, as described above, the controller 110 is configured or programmed to determine the values of the in-operation parameters $\tau_3$ of the servomotors M6*e* and M6*f* based on the operation speed $\omega$ with respect to the operation unit 120, and control the servomotors M6*e* and M6*f* to exert the in-operation assisting forces using the determined values of the in-operation parameters $\tau_3$. Accordingly, using the in-operation parameters $\tau_3$, the servomotors M6*e* and M6*f* can easily exert the in-operation assisting forces.

According to the first embodiment, as described above, the controller 110 is configured or programmed to linearly increase the absolute value of the in-operation parameter $\tau_3$ as the absolute value of the operation speed $\omega$ increases, and change the level of the in-operation assisting force by changing the magnitude of the in-operation parameter $\tau_3$ based on the level change operation of the operator. Accordingly, the magnitude of the in-operation parameter $\tau_3$ is changed according to the level change operation of the operator, and thus the level of the in-operation assisting force can be changed using the in-operation parameter $\tau_3$ that has been changed in magnitude.

According to the first embodiment, as described above, the controller 110 is configured or programmed to exert at least one of the operation start assisting force, the in-operation assisting force, or the braking force on at least one of a plurality of servomotors M6a to M6g. Accordingly, at least one of the level of the operation start assisting force, the level of the in-operation assisting force, or the level of the braking force for at least one of a plurality of rotation axes A1 to A7 can be changed to a desired level.

Second Embodiment

A braking parameter $\tau$ according to a second embodiment is now described with reference to FIGS. 29 and 30.

Figure 29:
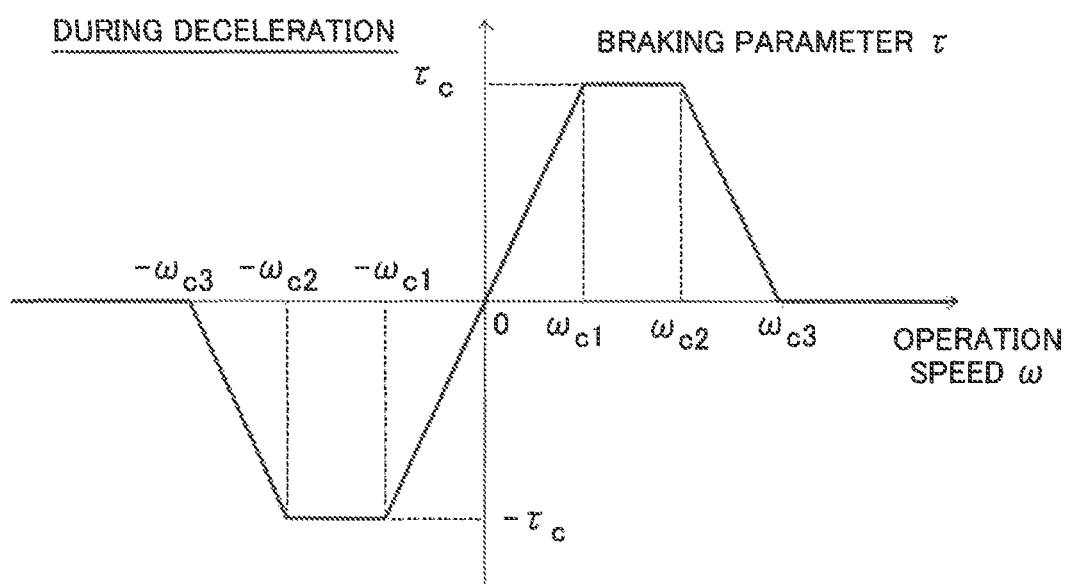
FIG. 29 is a diagram showing a braking parameter during deceleration according to a second embodiment.
Figure 30:
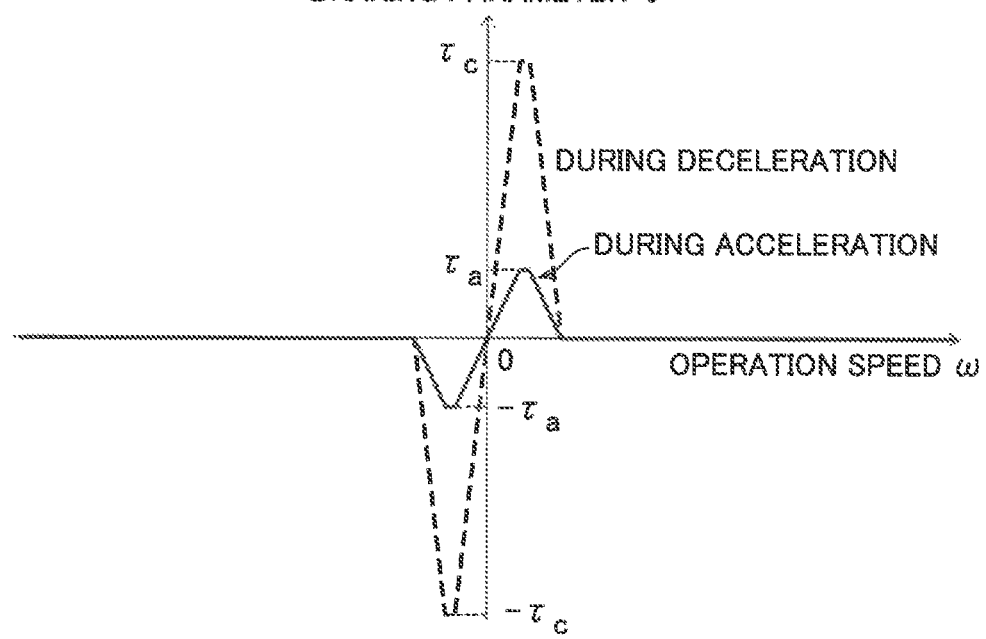
FIG. 30 is a diagram showing a braking parameter during acceleration and deceleration according to the second embodiment.

In the second embodiment, as shown in FIGS. 29 and 30, when an operation is decelerated, a controller 110 sets the braking parameter $\tau$ to zero when an operation speed $\omega$ is greater than a threshold $\omega_{c3}$, increases the braking parameter $\tau$ as the operation speed $\omega$ decreases when the operation speed $\omega$ is equal to or less than the threshold $\omega_{c3}$ and is greater than a threshold $\omega_{c2}$, sets the braking parameter $\tau$ to constant $\tau_c$ when the operation speed $\omega$ is equal to or less than the threshold $\omega_{c2}$ and is greater than a threshold $\omega_{c1}$, and decreases the braking parameter $\tau$ as the operation speed $\omega$ decreases when the operation speed $\omega$ is equal to or less than the threshold $\omega_{c1}$. Furthermore, when the operation is decelerated, the controller 110 sets the braking parameter $\tau$ to zero when the operation speed $\omega$ is less than a threshold $-\omega_{c3}$, decreases the braking parameter $\tau$ as the operation speed $\omega$ increases when the operation speed $\omega$ is equal to or greater than the threshold $-\omega_{c3}$ and is less than a threshold $-\omega_{c2}$, sets the braking parameter $\tau$ to constant $\tau_c$ when the operation speed $\omega$ is equal to or greater than the threshold $-\omega_{c2}$ and is less than a threshold $-\omega_{c1}$, and increases the braking parameter $\tau$ as the operation speed $\omega$ increases when the operation speed $\omega$ is equal to or greater than the threshold $-\omega_{c1}$.

When the operation speed $\omega$ is between the threshold value $\omega_{c3}$ and the threshold $\omega_{c2}$ and between the threshold $-\omega_{c3}$ and the threshold $-\omega_{c2}$, the absolute value of the braking parameter $\tau$ increases linearly. When the operation speed $\omega$ is between the threshold $\omega_{c1}$ and 0 and between the threshold $-\omega_{c1}$ and 0, the absolute value of the braking parameter $\tau$ decreases linearly. When the operation speed $\omega$ is 0, the braking parameter $\tau$ is 0. The braking parameter $\tau$ during acceleration according to the second embodiment is similar to the braking parameter $\tau$ according to the first embodiment shown in FIG. 21. That is, in the second embodiment, the braking parameter $\tau$ during acceleration and the braking parameter $\tau$ during deceleration change in the same manner. As shown in FIG. 30, the maximum $\tau_c$ of the absolute value of the braking parameter $\tau$ during deceleration is four times or more than the maximum $T_a$ of the absolute value of the braking parameter $\tau$ during acceleration. Also in the second embodiment, the level of a braking force during deceleration is changed by operating level selectors 23b1 to 23b4.

For example, as shown in FIG. 24, when the braking parameter $\tau$ during deceleration is a relatively large constant value $\tau_b$ as in the first embodiment at high speed, and the braking parameter $\tau$ during acceleration is 0 as in the first embodiment at high speed, there may be a sense of discomfort in operation of an operation unit 120 due to a large difference between the braking parameter $\tau$ during deceleration and the braking parameter $\tau$ during acceleration when the accelerated state and the decelerated state of the operation on the operation unit 120 are switched. Therefore, in the second embodiment, as shown in FIG. 30, the braking parameter $\tau$ during deceleration is set to 0 at high speed so as to be similar to the braking parameter $\tau$ during acceleration such that a sense of discomfort in operation can be significantly reduced when the accelerated state and the decelerated state are switched.

Third Embodiment

Figure 31:
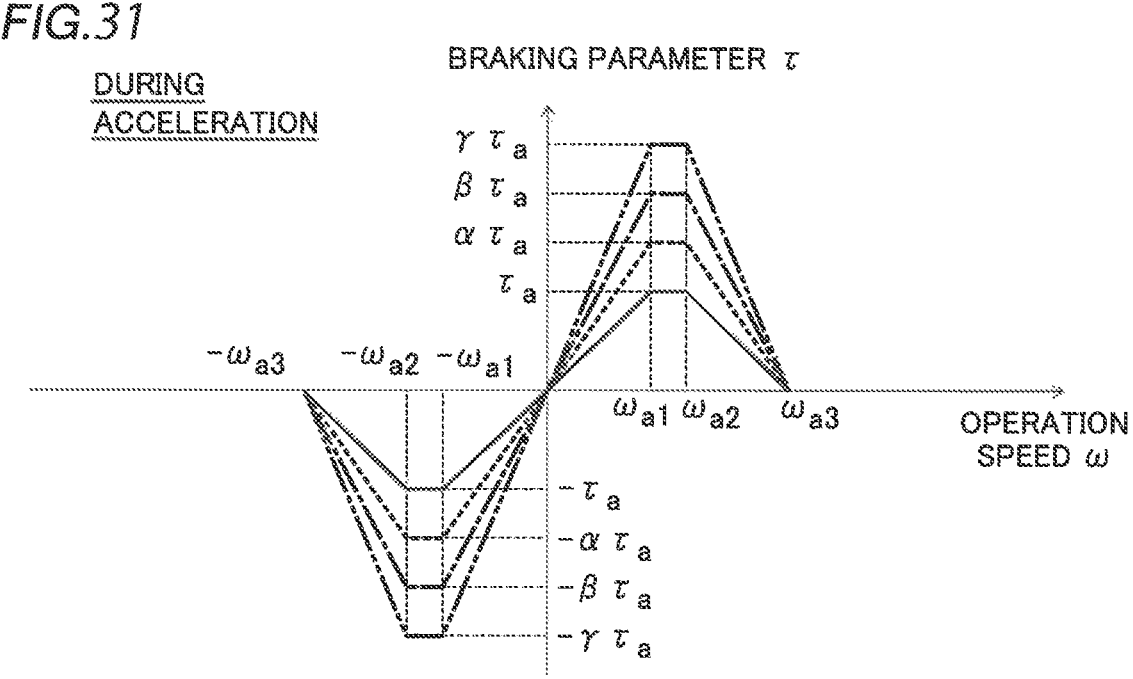
FIG. 31 is a diagram showing a braking parameter during acceleration according to a third embodiment.

A braking parameter $\tau$ according to a third embodiment is now described with reference to FIGS. 31 and 32.

In the third embodiment, a controller 110 changes the level of a braking force by changing the upper limit of the absolute value of the braking parameter $\tau$ based on the level change operation of an operator. Specifically, as shown in FIG. 31, when an operation is accelerated, a level selector 23b2 is pressed such that the controller 110 increases the braking parameter $\tau$ by $\alpha$ times the braking parameter $\tau$ in a case in which a level selector 23b1 is pressed. A level selector 23b3 is pressed such that the controller 110 increases the braking parameter $\tau$ by $\beta$ times the braking parameter $\tau$ in a case in which a level selector 23b1 is pressed. A level selector 23b4 is pressed such that the controller 110 increases the braking parameter $\tau$ by $\gamma$ times the braking parameter $\tau$ in a case in which a level selector 23b1 is pressed. Thus, the maximum $T_a$ of the absolute value of the braking parameter $\tau$ is changed to $\alpha\tau_a$, $\beta\tau_a$, or $\gamma\tau_a$. Note that $\alpha$, $\beta$, and $\gamma$ have a relationship of $1<\alpha<\beta<\gamma$. In the third embodiment, a threshold $\omega_{a1}$, a threshold $\omega_{a2}$, a threshold $-\omega_{a1}$, and a threshold $-\omega_{a2}$ are not changed.

Figure 32:
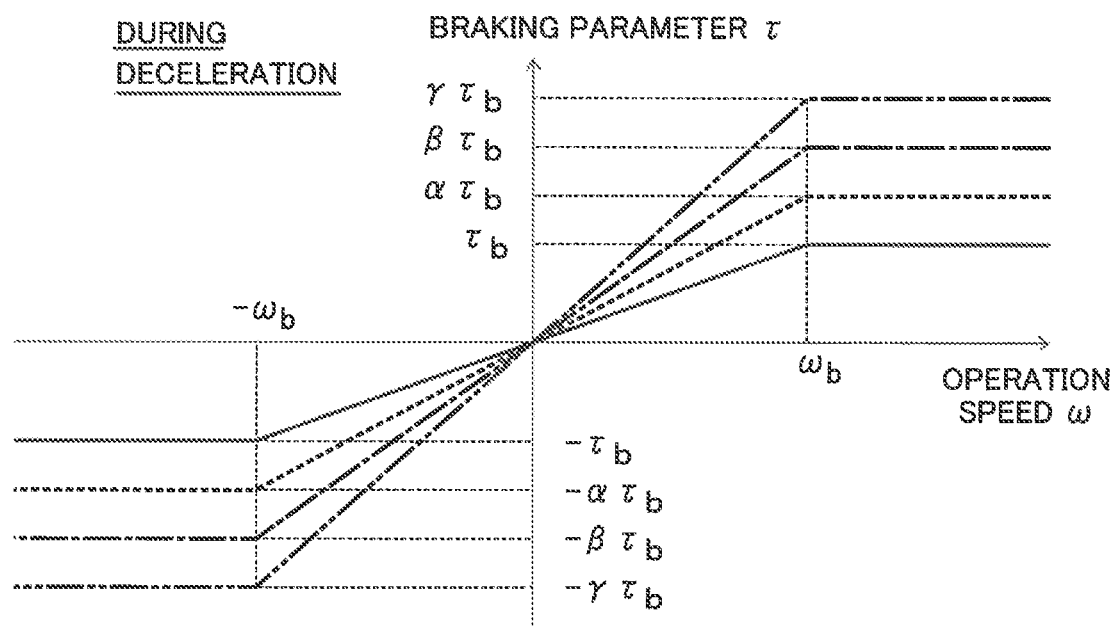
FIG. 32 is a diagram showing a braking parameter during deceleration according to the third embodiment.

As shown in FIG. 32, when the operation is decelerated, the level selector 23b2 is pressed such that the controller 110 increases the braking parameter $\tau$ by $\alpha$ times the braking parameter $\tau$ in a case in which the level selector 23b1 is pressed. The level selector 23b3 is pressed such that the controller 110 increases the braking parameter $\tau$ by $\beta$ times the braking parameter $\tau$ in a case in which the level selector 23b1 is pressed. The level selector 23b4 is pressed such that the controller 110 increases the braking parameter $\tau$ by $\gamma$ times the braking parameter $\tau$ in a case in which the level selector 23b1 is pressed. Thus, the maximum $\tau_b$ of the absolute value of the braking parameter $\tau$ is changed to $\alpha\tau_b$, $\beta\tau_b$, or $\gamma\tau_b$. In the third embodiment, a threshold $\omega_b$ and a threshold $-\omega_b$ are not changed. In the third embodiment, not only the maximum value of the braking parameter $\tau$ but also the slope of the braking parameter $\tau$ is changed.

Modified Examples

The embodiments disclosed this time must be considered as illustrative in all points and not restrictive. The scope of the present disclosure is not shown by the above description of the embodiments but by the scope of claims for patent, and all modifications or modified examples within the meaning and scope equivalent to the scope of claims for patent are further included.

For example, while all of the level of the operation start assisting force, the level of the in-operation assisting force, and the level of the braking force are changed based on the level change operation of the operator in each of the aforementioned first to third embodiments, the present disclosure is not limited to this. For example, one or two of the level of the operation start assisting force, the level of the in-operation assisting force, and the level of the braking force may alternatively be changed.

While the level change receiver 23a is arranged on the remote control apparatus 2 in each of the aforementioned first to third embodiments, the present disclosure is not limited to this. The level change receiver 23a may alternatively be arranged on an apparatus other than the remote control apparatus 2.

While the level change receiver 23a includes a touch panel in each of the aforementioned first to third embodiments, the present disclosure is not limited to this. For example, the level change receiver 23a may alternatively include a keyboard, a trackball, a mouse, a lever, a dial, a joystick, a foot switch, a push-button switch, and/or a combination thereof.

While the level selectors 23b1 to 23b4 are arranged in common for the operation start assisting force, the in-operation assisting force, and the braking force in each of the aforementioned first to third embodiments, the present disclosure is not limited to this. For example, the level selectors 23b1 to 23b4 may alternatively be arranged individually for each of the operation start assisting force, the in-operation assisting force, and the braking force.

While when the operation is accelerated, the braking parameter $\tau$ is set to zero when the operation speed $\omega$ is greater than the threshold $\omega_{a3}$ or less than the threshold $-\omega_{a3}$ in each of the aforementioned first to third embodiments, the present disclosure is not limited to this. For example, the braking parameter $\tau$ may alternatively be set to a value other than 0 when the operation speed $\omega$ is greater than the threshold $\omega_{a3}$ or less than the threshold $-\omega_{a3}$.

While the braking parameter $\tau$ becomes constant when the operation speed $\omega$ is between the threshold $\omega_{a1}$ and the threshold $\omega_{a2}$ and between the threshold $-\omega_{a1}$ and the threshold $-\omega_{a2}$ in each of the aforementioned first to third embodiments, the present disclosure is not limited to this. For example, the braking parameter $\tau$ may alternatively be decreased when the operation speed $\omega$ becomes greater than the threshold $\omega_{a1}$, and the braking parameter $\tau$ may alternatively be increased when the operation speed $\omega$ becomes less than the threshold $-\omega_{a1}$.

While the braking parameter $\tau$ becomes constant when the operation speed $\omega$ is between the threshold $\omega_{c1}$ and the threshold $\omega_{c2}$ and between the threshold $-\omega_{c1}$ and the threshold $-\omega_{c2}$ in the aforementioned second embodiment, the present disclosure is not limited to this. For example, the braking parameter $\tau$ may alternatively be decreased when the operation speed $\omega$ becomes greater than the threshold $\omega_{c1}$, and the braking parameter $\tau$ may alternatively be increased when the operation speed $\omega$ becomes less than the threshold $-\omega_{c1}$.

While the maximum of the absolute value of the braking parameter $\tau$ during deceleration of the operation is increased to greater than the maximum of the absolute value of the braking parameter $\tau$ during acceleration of the operation in each of the aforementioned first to third embodiments, the present disclosure is not limited to this. For example, the maximum of the absolute value of the braking parameter $\tau$ during deceleration of the operation may alternatively be the same as the maximum of the absolute value of the braking parameter $\tau$ during accelerating of the operation.

While the controller 110 of the remote control apparatus 2 performs a control to exert the operation start assisting force, the in-operation assisting force, and the braking force in each of the aforementioned first to third embodiments, the present disclosure is not limited to this. For example, a controller other than the controller 110 of the remote control apparatus 2 may alternatively perform a control to exert the operation start assisting force, the in-operation assisting force, and the braking force.

Figure 33:
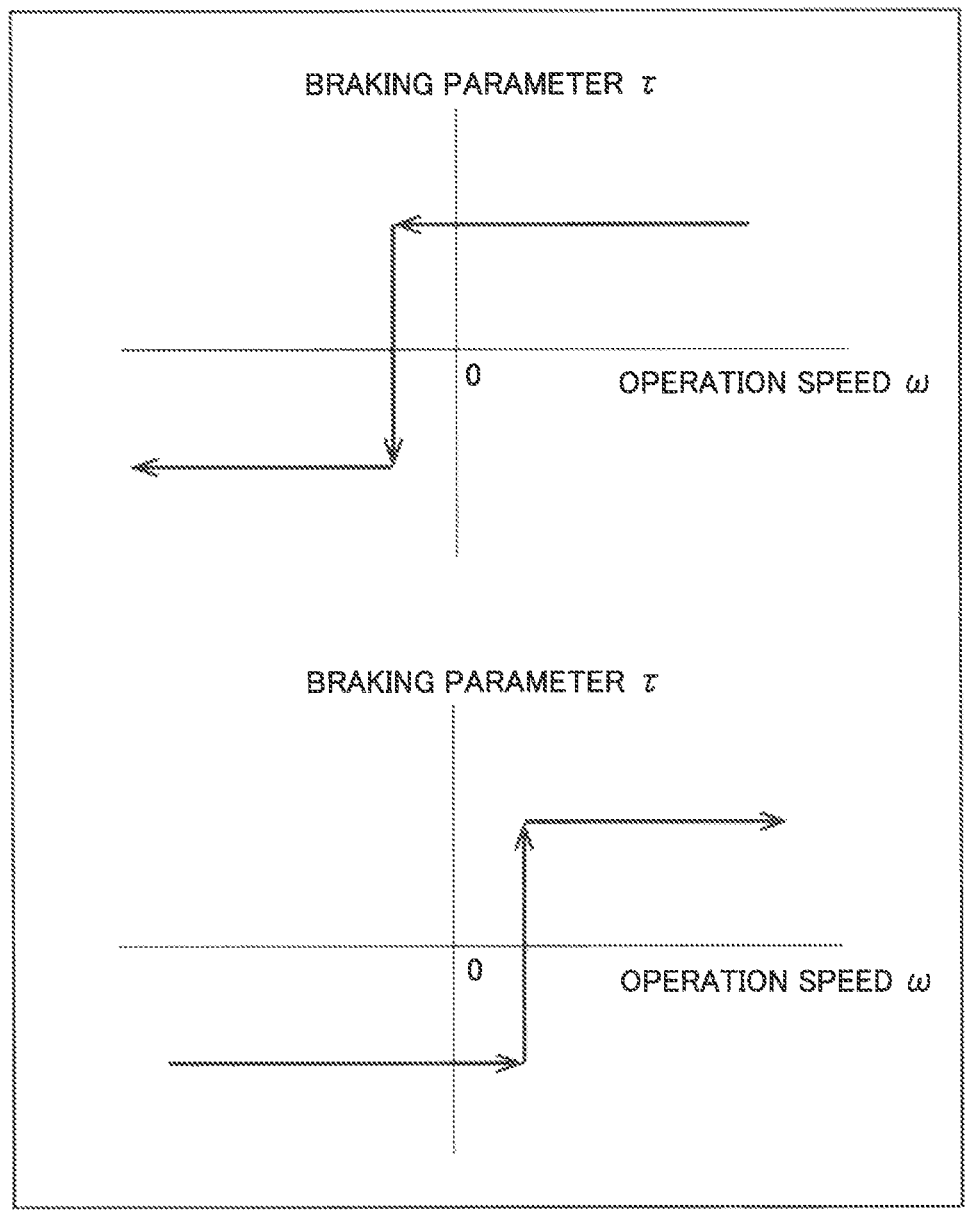
FIG. 33 is a diagram for illustrating a braking parameter during acceleration and deceleration according to a modified example.

While a change in the braking parameter $\tau$ is the same when the operation speed $\omega$ decreases and when the operation speed $\omega$ increases in each of the aforementioned first to third embodiments, the present disclosure is not limited to this. For example, the hysteresis as shown in FIG. 33 may alternatively be applied to the braking parameters $\tau$ according to the first and second embodiments. That is, the change in the braking parameter $\tau$ may be different when the operation speed $\omega$ changes from the positive side to the negative side and when the operation speed $\omega$ changes from the negative side to the positive side, and the braking parameter $\tau$ may not be changed near the operation speed $\omega$ of 0. Thus, even when the operation speed $\omega$ changes to vibrate to the positive side and the negative side near zero, the braking parameter $\tau$ does not change near the operation speed $\omega$ of 0, and thus it is possible to significantly reduce a sense of discomfort in operation. The sense of discomfort in operation refers to a sense of discomfort such as vibration, for example.

Figure 34:
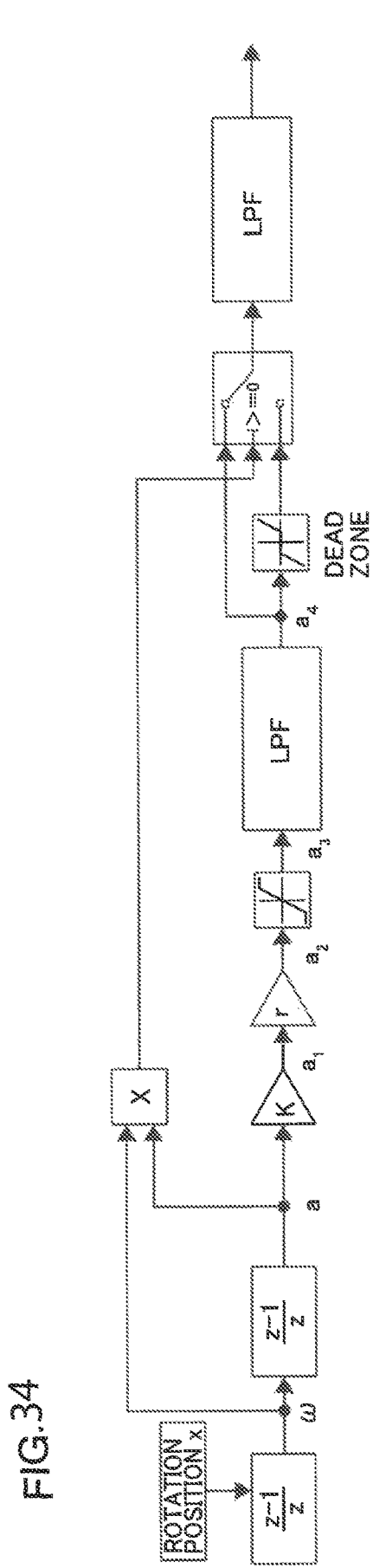
FIG. 34 is a control block diagram for generating an operation start assisting force according to the modified example.

Similarly, the operation start parameter $\tau_2$ may have a hysteresis. Specifically, as shown in FIG. 34, the controller 110 divides the calculated operation speed $\omega$ and operation acceleration a. When the result of division is 0 or more, the LPF is further applied to the post-LPF acceleration $a_4$, and the post-LPF acceleration $a_4$ to which the LPF has been further applied is output as the operation start parameter $\tau_2$. When the result of division is negative, a dead zone is applied to the post-LPF acceleration $a_4$, the LPF is further applied thereto, and the post-LPF acceleration $a_4$ to which the dead zone has been applied and the LPF has been further applied is output as the operation start parameter $\tau_2$.

In each of the aforementioned first to third embodiments, before and after switching of control cycles, the operation start parameter $\tau_2$, the in-operation parameter $\tau_3$, and the braking parameter $\tau$ may not be changed to a predetermined value or more. Thus, it is possible to significantly reduce a sense of discomfort in operation such as vibration due to large changes in the magnitudes of the operation start parameter $\tau_2$, the in-operation parameter $\tau_3$, and the braking parameter $\tau$.

While the number of levels of operation start assisting force, the number of levels of in-operation assisting force, and the number of levels of braking force are each four in each of the aforementioned first to third embodiments, the present disclosure is not limited to this. The number of levels of operation start assisting force, the number of levels of in-operation assisting force, and the number of levels of braking force may alternatively be other than four.

While the operation start parameter $\tau_2$ and the in-operation parameter $\tau_3$ change linearly in each of the aforementioned first to third embodiments, the present disclosure is not limited to this. For example, the operation start parameter $\tau_2$ and the in-operation parameter $\tau_3$ may alternatively change sinusoidally.

While four manipulator arms 60 are provided in each of the aforementioned first to third embodiments, the present disclosure is not limited to this. In the present disclosure, the number of manipulator arms 60 may alternatively be any number as long as at least one manipulator arm 60 is provided.

While each of the arm portion 61 and the positioner 40 includes a 7-axis articulated robot in each of the aforementioned first to third embodiments, the present disclosure is not limited to this. For example, each of the arm portion 61 and the positioner 40 may alternatively include an articulated robot having an axis configuration other than the 7-axis articulated robot. The axis configuration other than the 7-axis articulated robot refers to six axes or eight axes, for example.

While the medical manipulator 1 includes the medical cart 3, the positioner 40, and the arm base 50 in each of the aforementioned first to third embodiments, the present disclosure is not limited to this. For example, the medical manipulator 1 may not include the medical cart 3, the positioner 40, or the arm base 50, but may include only the manipulator arms 60.

While the operation handle 21 includes two operation handles including the operation handle 21L arranged on the left side and the operation handle 21R arranged on the right side in each of the aforementioned first to third embodiments, the present disclosure is not limited to this. For example, the operation handle 21 may alternatively include one or three or more operation handles.

The functionality of the elements disclosed herein may be implemented using circuitry or processing circuitry that includes general purpose processors, special purpose processors, integrated circuits, application specific integrated circuits (ASICs), conventional circuitry and/or combinations thereof that are configured or programmed to perform the disclosed functionality. Processors are considered processing circuitry or circuitry as they include transistors and other circuitry therein. In the present disclosure, the circuitry, units, or means are hardware that carries out or is programmed to perform the recited functionality. The hardware may be hardware disclosed herein or other known hardware that is programmed or configured to carry out the recited functionality. When the hardware is a processor that may be considered a type of circuitry, the circuitry, means, or units are a combination of hardware and software, and the software is used to configure the hardware and/or processor.

What is claimed is:

1. A robotic surgical system comprising:
    a patient-side apparatus including a manipulator arm having a tip end to which a surgical instrument is attached;
    an operator-side apparatus including an operation unit comprising an operation handle configured to receive an operator operation;
    a controller; and
    a level change receiver comprising a touch-panel or button configured to receive a level change operation; wherein
    the operation unit includes a drive to assist operation of the operation handle receiving the operator operation;
    the controller is configured or programmed to
        control the drive to exert at least one of an operation start assisting force exerted when the operation unit starts to be operated, an in-operation assisting force exerted when the operation unit is being operated, or a braking force exerted when the operation unit is stopped; and
    the controller is configured or programmed to
        change at least one of a level of the operation start assisting force, a level of the in-operation assisting force, or a level of the braking force based on the level change operation received by the level change receiver.

2. The robotic surgical system according to claim 1, wherein the controller is configured or programmed to:
    control the drive to exert all of: the operation start assisting force exerted when the operation unit starts to be operated; the in-operation assisting force exerted when the operation unit is being operated; and the braking force exerted when the operation unit is stopped; and
    change all of: the level of the operation start assisting force; the level of the in-operation assisting force; and the level of the braking force based on the received level change operation.

3. The robotic surgical system according to claim 1, wherein the level change receiver receives at least one of a change in the level of the operation start assisting force, a change in the level of the in-operation assisting force, or a change in the level of the braking force.

4. The robotic surgical system according to claim 3, wherein
    at least one of the operation start assisting force, the in-operation assisting force, or the braking force has a plurality of levels; and
    the level change receiver includes a plurality of level selectors corresponding to the plurality of levels.

5. The robotic surgical system according to claim 4, wherein
    the level change receiver further includes a level change target selector selecting a target to be changed in level from among the operation start assisting force, the in-operation assisting force, and the braking force; and
    the plurality of level selectors receive a level change for the target selected through the level change target selector.

6. The robotic surgical system according to claim 3, wherein the level change receiver is arranged on the operator-side apparatus.

7. The robotic surgical system according to claim 1, wherein the controller is configured or programmed to:
    determine a value of a braking parameter of the drive based on an operation acceleration and an operation speed with respect to the operation unit; and
    control the drive to exert the braking force using the determined value of the braking parameter.

8. The robotic surgical system according to claim 7, wherein the controller is configured or programmed to, when the operation is decelerated, maintain the braking parameter constant when an absolute value of the operation speed is greater than a deceleration threshold, decrease an absolute value of the braking parameter as the absolute value of the operation speed decreases when the absolute value of the operation speed is equal to or less than the deceleration threshold, and change the level of the braking force by changing an upper limit of the absolute value of the braking parameter based on the received level change operation.

9. The robotic surgical system according to claim 7, wherein the controller is configured or programmed to, when the operation is accelerated, increase an absolute value of the braking parameter as an absolute value of the operation speed increases when the absolute value of the operation speed is less than a first acceleration threshold, maintain the braking parameter constant when the absolute value of the operation speed is equal to or greater than the first acceleration threshold and is less than a second acceleration threshold, decrease the absolute value of the braking parameter as the absolute value of the operation speed increases when the absolute value of the operation speed is equal to or greater than the second acceleration threshold and is less than a third acceleration threshold, set the braking parameter to zero when the absolute value of the operation speed is equal to or greater than the third acceleration threshold, and change the level of the braking force by changing an upper limit of the absolute value of the braking parameter based on the level change operation of the operator.

10. The robotic surgical system according to claim 1, wherein the controller is configured or programmed to:
determine a value of an operation start parameter of the drive based on an operation acceleration with respect to the operation unit; and
control the drive to exert the operation start assisting force using the determined value of the operation start parameter.

11. The robotic surgical system according to claim 10, wherein the controller is configured or programmed to:
linearly increase an absolute value of the operation start parameter as an absolute value of the operation acceleration increases; and
change the level of the operation start assisting force by changing a magnitude of the operation start parameter with respect to the operation acceleration based on the received level change operation.

12. The robotic surgical system according to claim 1, wherein the controller is configured or programmed to:
determine a value of an in-operation parameter of the drive based on an operation speed with respect to the operation unit; and
control the drive to exert the in-operation assisting force using the determined value of the in-operation parameter.

13. The robotic surgical system according to claim 12, wherein the controller is configured or programmed to:
linearly increase an absolute value of the in-operation parameter as an absolute value of the operation speed increases; and
change the level of the in-operation assisting force by changing a magnitude of the in-operation parameter based on the received level change operation.

14. The robotic surgical system according to claim 1, wherein
the operation unit includes a plurality of rotation axes and a plurality of drives including the drive and provided so as to correspond to the plurality of rotation axes, respectively; and
the controller is configured or programmed to exert at least one of the operation start assisting force, the in-operation assisting force, or the braking force on at least one of the plurality of drives.

15. An operator-side apparatus to operate a patient-side apparatus including a manipulator arm having a tip end to which a surgical instrument is attached, the operator-side apparatus comprising:
an operation unit comprising an operation handle configured to receive an operator operation;
a controller; and
a level change receiver comprising a touch-panel or button configured to receive a level change operation; wherein the operation unit includes a drive to assist operation of the operation handle receiving the operator operation;
the controller is configured or programmed to
control the drive to exert at least one of an operation start assisting force exerted when the operation unit starts to be operated, an in-operation assisting force exerted when the operation unit is being operated, or a braking force exerted when the operation unit is stopped; and
the controller is configured or programmed to
change at least one of a level of the operation start assisting force, a level of the in-operation assisting force, or a level of the braking force based on the level change operation received by the level change receiver.

16. A control method of a robotic surgical system, the robotic surgical system comprising a patient-side apparatus including a manipulator arm having a tip end to which a surgical instrument is attached and an operator-side apparatus including an operation unit comprising an operation handle configured to receive an operator operation, the control method comprising:
receiving at least one of a change in a level of an operation start assisting force exerted when the operation unit starts to be operated, a change in a level of an in-operation assisting force exerted when the operation unit is being operated, or a change in a level of a braking force exerted when the operation unit is stopped; and
exerting at least one of the operation start assisting force, the in-operation assisting force, or the braking force corresponding to a changed level.

17. The control method of the robotic surgical system according to claim 16, wherein the receiving of the change in the level includes receiving all of the change in the level of the operation start assisting force exerted when the operation unit starts to be operated, the change in the level of the in-operation assisting force exerted when the operation unit is being operated, and the change in the level of the braking force exerted when the operation unit is stopped.

18. The control method of the robotic surgical system according to claim 16, wherein the receiving of at least one of the changes in the levels includes receiving at least one of the change in the level of the operation start assisting force, the change in the level of the in-operation assisting force, or the change in the level of the braking force by a level change receiver.

19. The control method of the robotic surgical system according to claim 18, wherein
at least one of the operation start assisting force, the in-operation assisting force, or the braking force has a plurality of levels; and
the level change receiver includes a plurality of level selectors corresponding to the plurality of levels.

20. The control method of the robotic surgical system according to claim 19, wherein
the level change receiver further includes a level change target selector for the operator to select a target to be changed in level from among the operation start assisting force, the in-operation assisting force, and the braking force; and
the plurality of level selectors receive a level change for the target selected through the level change target selector.

* * * * *